United States Patent
Lineaweaver et al.

(10) Patent No.: US 8,355,794 B2
(45) Date of Patent: *Jan. 15, 2013

(54) USING A GENETIC ALGORITHM IN MIXED MODE DEVICE

(75) Inventors: Sean Lineaweaver, Parker, CO (US); Gregory Wakefield, Ann Arbor, MI (US); Christopher van den Honert, Aurora, CO (US); Aaron Parkinson, Parker, CO (US); Wendy Parkinson, Parker, CO (US); Jim Patrick, Roseville (AU); John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 185 days.

This patent is subject to a terminal disclaimer.

(21) Appl. No.: 12/835,428

(22) Filed: Jul. 13, 2010

(65) Prior Publication Data

US 2010/0280307 A1 Nov. 4, 2010

Related U.S. Application Data

(63) Continuation-in-part of application No. 10/963,594, filed on Oct. 14, 2004, which is a continuation-in-part of application No. 10/385,880, filed on Mar. 11, 2003, now Pat. No. 6,879,860.

(51) Int. Cl.
*A61N 1/00* (2006.01)
(52) U.S. Cl. .................................. 607/57
(58) Field of Classification Search ......... 607/55–57
See application file for complete search history.

(56) References Cited

U.S. PATENT DOCUMENTS

| | | | |
|---|---|---|---|
| 4,532,930 A | 8/1985 | Crosby et al. | |
| 4,953,112 A | 8/1990 | Widin et al. | |
| 5,095,904 A | 3/1992 | Seligman et al. | |
| 5,277,694 A | 1/1994 | Leysieffer et al. | |
| 5,626,629 A | 5/1997 | Faltys et al. | |
| 6,157,861 A | 12/2000 | Faltys et al. | |
| 6,697,674 B2 * | 2/2004 | Leysieffer | 607/57 |
| 7,343,021 B2 | 3/2008 | Takagi et al. | |
| 2002/0176584 A1 | 11/2002 | Kates | |
| 2003/0133578 A1 | 7/2003 | Durant | |

(Continued)

FOREIGN PATENT DOCUMENTS

JP 09-325773 12/1997

(Continued)

OTHER PUBLICATIONS

Hideyuki Takagi, IEC-based Hearing Aid Fitting, IEEE SM C' 99 Conference Proceedings, Oct. 1999, vol. 3, 657-662 (6 pages).

(Continued)

*Primary Examiner* — Scott Getzow
(74) *Attorney, Agent, or Firm* — Kilpatrick, Townsend & Stockton, LLP.

(57) ABSTRACT

Apparatus and method for at least partially fitting a medical implant system to a recipient is described. The medical implant system is configured to provide electrical stimulation and at least one other mode of stimulation to the recipient. These apparatuses and methods comprise executing a genetic algorithm to select a set of parameter values for the medical implant system. This genetic algorithm may comprise generating successive generations of child populations and then providing a determined set of parameter values to the medical implant system for use in providing stimulation to the recipient.

28 Claims, 12 Drawing Sheets

U.S. PATENT DOCUMENTS

| | | | |
|---|---|---|---|
| 2005/0107845 | A1 | 5/2005 | Wakefield et al. |
| 2005/0129262 | A1 | 6/2005 | Dillon et al. |
| 2008/0165978 | A1 | 7/2008 | Cronin et al. |
| 2010/0152813 | A1 | 6/2010 | Lineaweaver et al. |
| 2011/0060383 | A1 | 3/2011 | Lineaweaver et al. |
| 2011/0060702 | A1 | 3/2011 | Lineaweaver |

FOREIGN PATENT DOCUMENTS

| | | |
|---|---|---|
| JP | 11-513539 | 11/1999 |
| JP | 2003-6171 | 1/2003 |
| WO | WO 2007/090243 | 8/2007 |

OTHER PUBLICATIONS

International Search Report for International Application No. PCT/US04/07400 mailed Aug. 27, 2004 (1 page).

Written Opinion for International Application No. PCT/US04/07400 mailed Aug. 27, 2004 (1 page).

International Search Report for International Application No. PCT/IB2010/054105 mailed Jun. 14, 2011 (5 pages).

European Official Communication for European Application No. 04 719 779.3 mailed Apr. 20, 2011 (3 pages).

Canadian Intellectual Property Office, "Office Action," issued in connection with Canadian Patent Application Serial No. 2,518,997, on Apr. 16, 2010 (2 pages).

Forrest, Stephanie, "Genetic Algorithms: Principles of Natural Selection Applied to Computation," Science, Aug. 13, 1993, vol. 261 (5123), pp. 872-878.

Takagi, Hideyuki, "Interactive Evolutionary Computation: Fusion of the Capabilities of EC Optimization and Human Evaluation," Proceedings of the IEEE, Sep. 2001, vol. 89, No. 9, pp. 1275-1296.

Skinner, et al., "Speech Recognition with the Nucleus 24 SPEAK, ACE, and CIS Speech Coding Strategies in newly Implanted Adults," Ear & Hearing, vol. 23, No. 3, 208-223, (Jun. 2002) (17 pages).

Skinner, et al., "Nucleus 24 Advanced Encoder Conversion Study: Performance versus Preference," Ear & Hearing, vol. 23, No. 18, 3S-7S, (Feb. 2002) (16 pages).

Wakefield, et al., "Recipient-Directed Design of Speech processor MAPs," in R.T. Miyamoto, ed., Cochlear Implants, Elsevier, International Congress Series, 1273 178-182 (2004) (5 pages).

Wakefield, et al., "Genetic Algorithms for Adaptive Psychopysical Procedures: Recipient-Directed Design of Speech-Processor MAPs," Ear & Hearing, 52S-72S, (Aug. 2005) (16 pages).

Japanese Office Action for Japanese Application No. 2006-507068 mailed on Jun. 1, 2010 along with English translation (4 pages).

Japanese Office Action for Japanese Application No. 2006-507068 mailed on Mar. 8, 2011 along with English translation (3 pages).

Japanese Office Action for Japanese Application No. 2006-507068 mailed on Oct. 18, 2011 along with English translation (5 pages).

\* cited by examiner

ACOUSTIC STIMULATION FREQUENCY BANDS

ELECTRICAL STIMULATION FREQUENCY BANDS

USING A GENETIC ALGORITHM IN MIXED MODE DEVICE

CROSS-REFERENCE TO RELATED APPLICATIONS

This application is a continuation-in-part of and claims priority to U.S. patent application Ser. No. 10/963,594, entitled "Using a Genetic Algorithm to Fit a Cochlear implant System to a Recipient," filed Oct. 14, 2004, which is a continuation-in-part of and claims priority to U.S. Pat. No. 6,879,860, entitled "Cochlear Implant Map Optimization With Use Of A Genetic Algorithm," filed Mar. 11, 2003, the entire contents and disclosures of each are hereby incorporated by reference.

This application is also related to PCT Application No. PCT/US2004/007400, U.S. Pat. Nos. 4,532,930, 5,277,694, 6,123,660, 6,162,169, 6,537,200, 6,565,503, 6,575,894, 6,697,674, U.S. patent application Ser. No. 12/557,233, entitled "Using a Genetic Algorithm Employing An Expedited Convergence Mechanism," filed Sep. 10, 2009, U.S. patent application Ser. No. 12/557,208, entitled "Using a Genetic Algorithm to Fit a Medical Implant System to a Patient," filed Sep. 10, 2009, and U.S. patent application Ser. No. 12/557,218, entitled "Using a Genetic Algorithm Employing Dynamic Mutation," filed Sep. 10, 2009. The entire disclosure and contents of the above patents are hereby incorporated by reference herein.

BACKGROUND

1. Field of the Invention

The present invention relates generally to stimulating medical devices, and more particularly, to fitting a stimulating medical device.

2. Related Art

Many medical devices have structural and/or functional features which are to be adjusted for an individual recipient. The process by which a medical device is tailored or customized for the specific needs of a recipient is commonly referred to as fitting. One type of medical device which is typically fitted to individual recipients is a cochlear implant system.

Cochlear implant systems provide the benefit of hearing to individuals suffering from severe to profound hearing loss. Hearing loss in such individuals is often due to the absence or destruction of the hair cells in the cochlea which transduce acoustic signals into nerve impulses. Cochlear implant systems essentially simulate the auditory nerves by directly delivering electrical stimulation to the auditory nerve fibers. This causes the brain to perceive a hearing sensation resembling the natural hearing sensation normally delivered by the auditory nerve.

Conventional cochlear implant systems commonly include an external assembly directly or indirectly attached to the body of the recipient (sometimes referred to herein as the recipient), and an internal assembly which is implanted in the recipient. The external assembly typically comprises one or more microphones for detecting sound, a speech processing unit that converts detected sound into an electrical coded signal, a power source, and an external transcutaneous transfer coil. The internal assembly typically comprises an internal transcutaneous transfer coil, a stimulator unit located within a recess of the temporal bone of the recipient, and an electrode array positioned in the recipient's cochlea. Completely implantable cochlear implant systems having functionally similar components are under development.

In addition to providing electrical stimulation, some cochlear implant systems also include a mechanical stimulation mode of operation. Such so called mixed-mode systems offer rehabilitation by mechanically stimulating a portion of a recipient's auditory pathway, either acoustically or physically. For example, there have been approaches to offer rehabilitation with conventional hearing aids via the application of an amplified acoustic signal to the external auditory canal, or by physically stimulating an ossicle of the middle ear or the inner ear via mechanical or hydromechanical stimulation.

Modern cochlear implant systems provide a wide variety of fitting options that can be customized for an individual recipient. Because recipients are heterogeneous, each recipient requires a different set of parameters to maximize speech reception and recipient satisfaction. The task of the clinical professional, usually an audiologist, is to select a set of parameters, commonly referred to as a parameter map or, more simply, a MAP, that will provide the best possible sound reception for an individual recipient. Because there may be thousands of possible parameter maps, it is impractical for a recipient to experience all of the alternatives and to evaluate the performance of each alternative. Nor is it possible to identify an optimal parameter map by prescription based on a limited set of measurements as is, for example, the case in fitting eyeglasses. Because parameters of cochlear implant systems often interact non-linearly and non-monotonically, it is also not feasible to sequentially optimize individual parameters, adjusting each in succession to its optimal value.

As a result, clinicians have adopted a variety of approaches for fitting the cochlear implant systems to recipients. Some simply set the parameters to default values regardless of the individual recipients. Others adopt preferred parameter maps, which they believe are good, if not best, for many or most recipients. The preferences may be based on personal experience, published performance data, or intuition. Some clinicians evaluate a limited set of alternatives adjusting individual parameters based upon measured perceptual limitations and inferred relationships among the parameters. These approaches are time consuming, costly, and unreliable, and typically fail to achieve the optimal outcome for individual recipients.

SUMMARY

In one aspect of the present invention there is provided a method for at least partially fitting a medical implant system comprising a system for providing multiple modes of stimulation to a recipient, wherein each mode of stimulation comprises at least one fitting parameter, the method comprising: executing a genetic algorithm to select a determined value set comprising values for at least one fitting parameter for electrical stimulation and at least one parameter for another mode of stimulation, the genetic algorithm comprising: presenting signals processed by a plurality of value sets to the recipient using the medical implant system; receiving recipient feedback in response to the presented signals processed by the value sets; selecting, based on the recipient feedback, one or more of the presented value sets; and generating a successive generation of value sets using the selected one or more value sets; and providing the determined value set to the medical implant system for use in providing electrical and the other mode stimulation to the recipient.

In another aspect of the present invention, there is provided a system for at least partially fitting a mixed mode medical implant system to a recipient, wherein the mixed mode medical implant system is configured to provide electrical stimulation and an other mode of stimulation to the recipient, the system comprising: a processor configured to execute a genetic algorithm to select a determined value set comprising values for at least one parameter for providing electrical stimulation and at least one parameter for providing the other mode of stimulation, wherein the processor in executing the genetic algorithm is configured to present signals processed by a plurality of value sets to the recipient using the medical implant system, receive recipient feedback in response to the presented signals, select, based on the recipient feedback, one or more of the value sets, and generate a successive generation of value sets using the selected one or more value sets; and an interface configured to provide at least one of the value sets to the medical implant system for use by the medical implant system in providing stimulation to the recipient.

In another aspect of the present invention, there is provided a system for at least partially fitting a medical implant system for providing multiple modes of stimulation to a recipient, wherein each mode of stimulation comprises at least one fitting parameter, the system comprising: means for executing a genetic algorithm to select a determined value set comprising values for at least one fitting parameter for electrical stimulation and at least one parameter for another mode of stimulation, the genetic algorithm comprising: means for presenting signals processed by a plurality of value sets to the recipient using the medical implant system; means for receiving recipient feedback in response to the presented signals processed by the value sets; means for selecting, based on the recipient feedback, one or more of the presented value sets; and means for generating a successive generation of value sets using the selected one or more value sets; and means for providing the determined value set to the medical implant system for use in providing electrical and the other mode stimulation to the recipient.

BRIEF DESCRIPTION OF THE DRAWINGS

Embodiments of the present invention are described below with reference to the attached drawings, in which.

DETAILED DESCRIPTION

Aspects of the present invention are generally directed to the use of a genetic algorithm in fitting a mixed mode stimulating medical device. In an embodiment the mixed mode stimulating medical device is configured to apply electrical stimulation and at least one other mode of stimulation. This other mode of stimulation may comprise acoustic and/or mechanical stimulation.

Embodiments of the present invention are described herein primarily in connection with one type of implantable medical device, a hearing prosthesis, namely a cochlear prosthesis (commonly referred to as cochlear prosthetic devices, cochlear implants, cochlear devices, and the like; simply "cochlea implants" herein.) Cochlear implants deliver electrical stimulation to the cochlea of a recipient. As used herein, cochlear implants also include hearing prostheses that deliver electrical stimulation in combination with other modes of stimulation, such as acoustic or mechanical stimulation (sometimes referred to as mixed-mode devices). It would be appreciated that embodiments may also be implemented in any cochlear implant or other hearing prosthesis now known or later developed. For example, in an embodiment electrical stimulation may be provided via an auditory brain stimulator.

Figure 1:
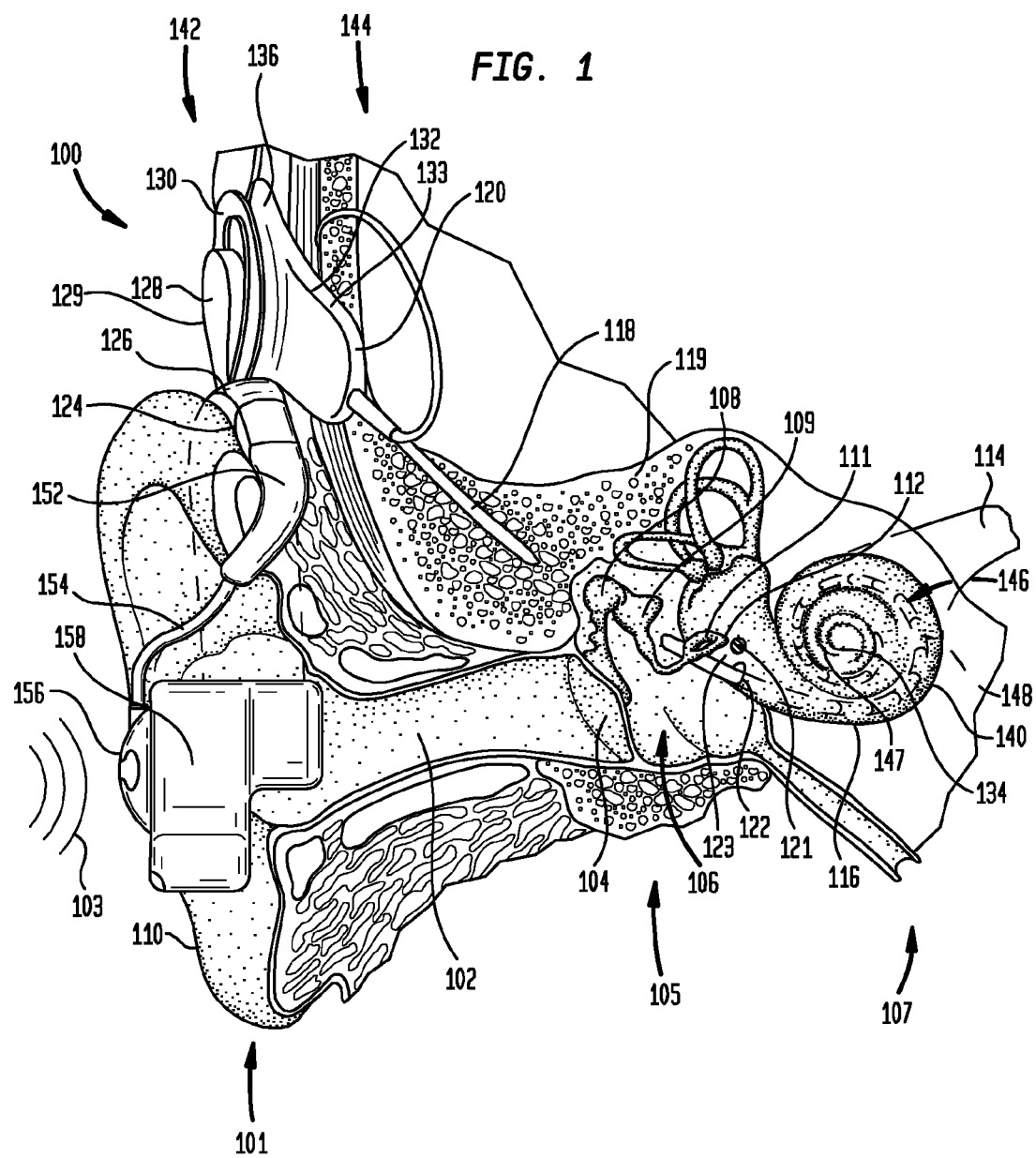
FIG. 1 is a schematic diagram of an exemplary cochlear implant system which may be fitted to an individual recipient in accordance with an embodiment.
Figure 2:
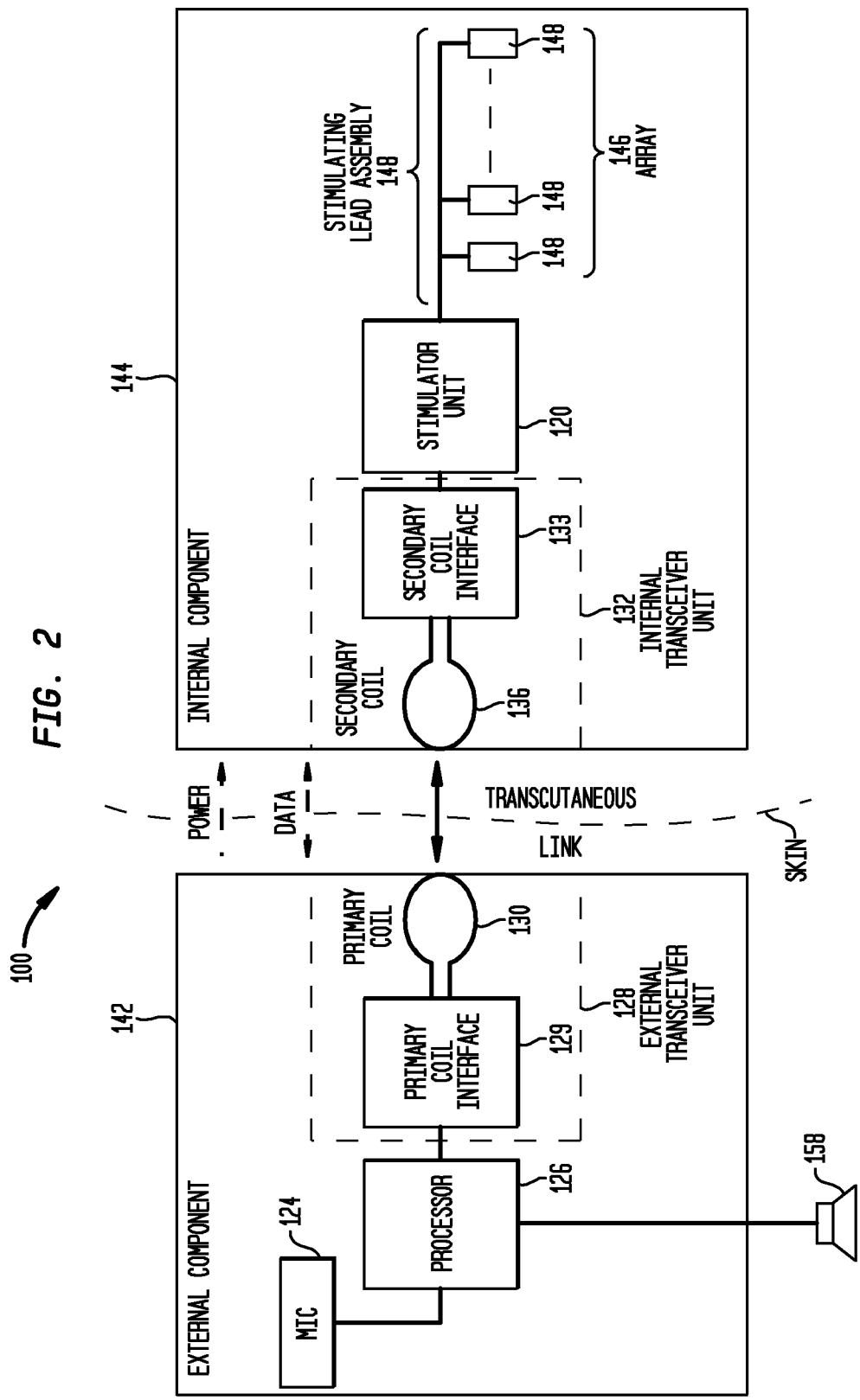
FIG. 2 is a functional block diagram of the cochlear implant of FIG. 1, in accordance with an embodiment of the present invention.

FIG. 1 is perspective view of a cochlear implant, referred to as cochlear implant system 100 implanted in a recipient, in accordance with an embodiment of the present invention. FIG. 2 is a functional block diagram of cochlear implant 100. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant system 100 comprises an external component 142 which is directly or indirectly attached to the body of the recipient, and an internal component 144 which is temporarily or permanently implanted in the recipient. External component 142 is often referred as a sound processor device that typically comprises one or more sound input elements, such as microphone 124 for detecting sound, a processor 126, a power source (not shown), and an external transceiver unit 128. External transceiver unit 128 comprises an external coil interface 129 (also referred to herein as primary coil interface 129), an external coil 130 (also referred to herein as primary coil 130) and, preferably a magnet (not shown) secured directly or indirectly concentric to internal coil 136 (also referred to herein as secondary coil 136). External and internal coils are closely coupled enabling power and data transfers by inductive link. Processor 126 processes the output of microphone 124 that is positioned, in the depicted embodiment, behind the ear of the recipient. Processor 126 generates encoded signals, sometimes referred to herein as encoded data signals, which are provided to the external coil interface 129 via a cable (not shown).

The internal implant component 144 comprises an internal coil 136 (also referred to herein as secondary coil 136), an implant unit 134, and a stimulating lead assembly 118. As illustrated, internal transceiver unit 132 comprises an internal coil interface 133 (also referred to as secondary coil interface 132), an internal coil 136 (also referred to herein as secondary coil 136). Secondary coil interface 133 is connected to the secondary coil 136. Secondary coil 136 may include a magnet (also not shown) fixed in the middle of secondary coil 136. The stimulator unit 120 may be hermetically sealed within a biocompatible housing. The internal coil 136 receives power and stimulation data from primary coil 130.

Stimulating lead assembly 118 has a proximal end connected to stimulator unit 120, and a distal end implanted in cochlea 140. Stimulating lead assembly 118 extends from stimulator unit 120 to cochlea 140 through mastoid bone 119. In some embodiments stimulating lead assembly 118 may be implanted at least in basal region 116, and sometimes further. For example, stimulating lead assembly 118 may extend towards apical end of cochlea 140, referred to as cochlea apex 147. In certain circumstances, stimulating lead assembly 118 may be inserted into cochlea 140 via a cochleostomy 122. In other circumstances, a cochleostomy may be formed through round window 121, oval window 112, the promontory 123 or through an apical turn 135 of cochlea 140.

Stimulating lead assembly 118 comprises a longitudinally aligned and distally extending array 146 of electrode contacts 148, sometimes referred to as array of electrode contacts 146 herein. Although array of electrode contacts 146 may be disposed on Stimulating lead assembly 118, in most practical applications, array of electrode contacts 146 is integrated into Stimulating lead assembly 118. As such, array of electrode contacts 146 is referred to herein as being disposed in Stimulating lead assembly 118. Stimulator unit 120 generates stimulation signals which are applied by electrode contacts 148 to cochlea 140, thereby stimulating auditory nerve 114.

In cochlear implant system 100, primary coil 130 transfers electrical signals (that is, power and stimulation data) to the internal or secondary coil 136 via an inductive coupled radio frequency (RF) link. Secondary coil 136 is typically made of multiple turns of electrically insulated single-strand or multistrand platinum or gold wire. The electrical insulation of secondary coil 136 is provided by a biocompatioble wire insulator and a flexible silicone molding (not shown). In use, secondary coil 136 may be positioned in a recess of the temporal bone adjacent auricle 110 of the recipient.

In addition to providing electrical stimulation, cochlear implant 100 is also configured for application of acoustic stimulation. As illustrated, sound processor 126 is connected to an ear hook 152 that connects sound processor 126 to an ear mold 156 via a cable 154. In the presently illustrated embodiment, ear mold 156 comprises a loudspeaker (also referred to as a receiver) for providing acoustic stimulation to the recipient. Because in this example, speaker 158 is located in ear mold 156 it is referred to as a Receiver in the ear (RITE) device. Ear mold 156 may be custom fit to the recipient's ear canal and be a standard type of ear mold used in conventional RITE devices. It should be noted, however, that other types of configurations may be used for providing acoustic stimulation to the recipient. For example, in an alternative embodiment, a loudspeaker may instead be located in sound processor 126 and sound channeled to the ear mold 156 via a tube, such as in a behind the ear (BTE) hearing aid.

Sound processor 126 may perform an audio spectral analysis of acoustic signals received by microphone 124 to obtain a plurality of output channel amplitudes. As will be discussed in further detail below, sound processor 126 may analyze these channel amplitudes in determining the electrical and acoustic stimulation to be provided to the recipient. For example, in an embodiment, acoustic stimulation may be provided via loudspeaker 158 for frequencies below a particular cut-off frequency and electrical stimulation may be provided via stimulating lead assembly 118 for frequencies above a particular cut-off frequency. These cut-off frequencies may be parameters that may be individually specified and adjusted for the recipient. Performing two types of stimulation is referred to herein as bi-modal stimulation.

Providing acoustic and electrical stimulation may advantageously use the residual natural hearing capability of the recipient if any exists, while supplementing this natural hearing with electrical stimulation. This electrical stimulation may be used to convey sound information that is only partially conveyed or is not conveyed by the natural hearing of recipient.

In cochlear implant 100, there may be a substantial number of parameters which may be customized to optimally fit a cochlear implant system to an individual recipient. The selected subset of parameters and their respective values is collectively and generally referred to herein as a "parameter map," a "cochlear map" or "MAP." A "MAP" is also sometimes referred to as a "program." In an embodiment, the MAP may specify values for a subset of parameters for application of electrical stimulation as well as parameters for application of another mode (e.g., mechanical or acoustic) of stimulation.

Examples of electrical stimulation parameters that may be specified by the MAP include, for example, the speech strategy implemented in the cochlear implant system. Additionally, within any given speech strategy a great many parameters and parameter values may be specified to tailor the encoding and stimulation for an individual recipient. Examples of parameters and parameter values that may be selected for a speech strategy include but are not limited to the number of channels of stimulation represented, the configuration and number of intracochlear and/or extracochlear electrodes which are to be associated with each channel, the pulse repetition rate for each channel, the pulse pattern, the width of each pulse or between pulses, the number of spectral maxima periodically chosen for representation, the mapping of sound pressure to stimulus current for each channel (threshold levels, comfort levels and compression curves), frequency boundaries allocated for each channel, front end filtering of the audio from the microphone (pre-emphasis), and automatic gain control threshold, channel-specific compression ratios, and attack and release times. In an embodiment, a subset of these parameters may be selected for obtaining values with the genetic algorithm.

In a multi-modal device configured for application of acoustic stimulation, the MAP may also specify acoustic stimulation parameters. Examples of exemplary acoustic stimulation parameters include parameters specifying the frequencies for which acoustic stimulation is to be applied, the filter response(s) used for processing the sound in applying acoustic stimulation, the gain to be applied to the signal in applying acoustic stimulation. For example, in an embodiment, the MAP may comprise parameters specifying the frequency boundaries for filters used in filtering the signal from the microphone, the transfer functions for the filters, as well as the slopes of each band-pass filter.

For example, in an embodiment, the MAP may comprise parameters specifying which electrodes are to be active and which are to remain inactive, as well as the frequency allocation of each active electrode. These parameters may further specify the frequency range for the signal to be provided via the loudspeaker as well as the transfer function for filtering this signal. These parameters may be selected so as to optimize the combinatory hearing.

Additional parameters that may be specified by the MAP may include time domain parameters. Such parameters include, for example, adjusting electrical periodicity of pulse timing to be synchronized with the mechanical signal fluctuations, adjusting delays in the electrical stimulus to compensate for missing propagation delays of various middle ear and inner ear pathways, etc.

Figure 3:
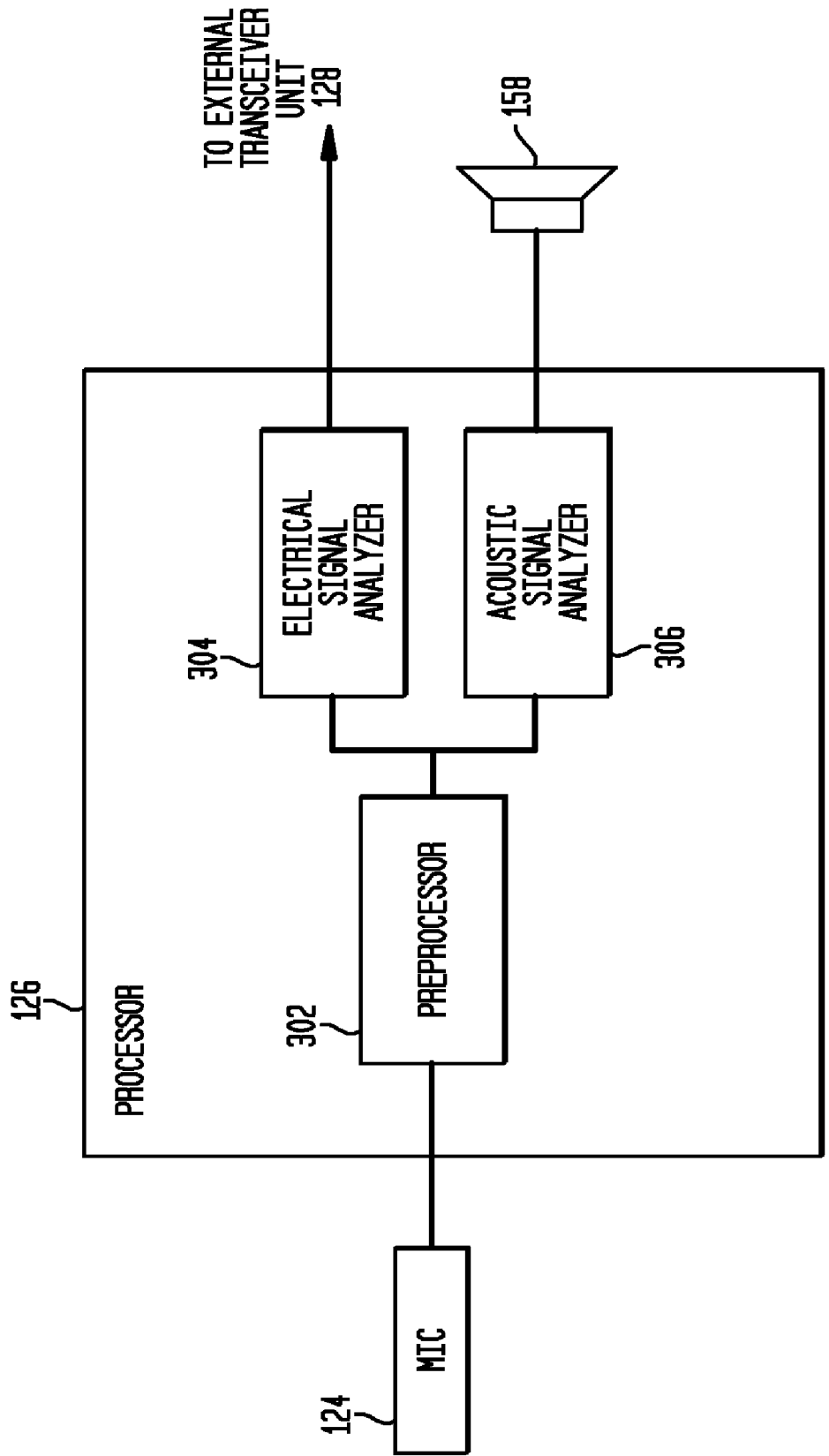
FIG. 3 is a functional block diagram of one embodiment for implementing a sound processor for a bimodal hearing prosthesis capable of applying acoustic stimulation and electrical stimulation to a cochlea, in accordance with an embodiment of the present invention.

In the an embodiment, the values of the parameters (referred to as parameter values) in the MAP may be selectable options, such as whether a particular function (e.g., noise filtering) is programmed on or off, or which of particular predetermined set of options are to be used (e.g., whether to apply ACE, SPEAK, F0, F1, F2, or the MPEAK speech strategy). As one or ordinary skill in the art would appreciate, the above parameters are an example of mixed-mode parameters which may be selected and tailored to optimally fit a mixed-mode (electrical and mechanical stimulation, or electrical and acoustic stimulation) cochlear implant system to a recipient, and in other embodiments other parameters may be included in the MAP FIG. 3 is a functional block diagram of one embodiment for implementing a sound processor for a bimodal hearing prosthesis capable of applying acoustic stimulation and electrical stimulation to a cochlea, in accordance with an embodiment. A microphone 126 detects sound signals and passes corresponding electrical signals to a preprocessor 302. Preprocessor 302 filters the electrical signals and passes signal component(s) in a first frequency sub-band to an electrical signal analyzer 304, and passes signal component(s) in a second frequency sub-band to an acoustic signal analyzer 306. In this embodiment the first frequency sub-band comprises a high frequency portion of the audible frequency spectrum, which corresponds to a basal region of a cochlea adjacent to which an electrode array has been positioned. The second frequency sub-band comprises a low frequency portion of the audible frequency spectrum, which corresponds to an apical region of the cochlea in which residual natural hearing of the cochlea has been retained.

Figure 4:
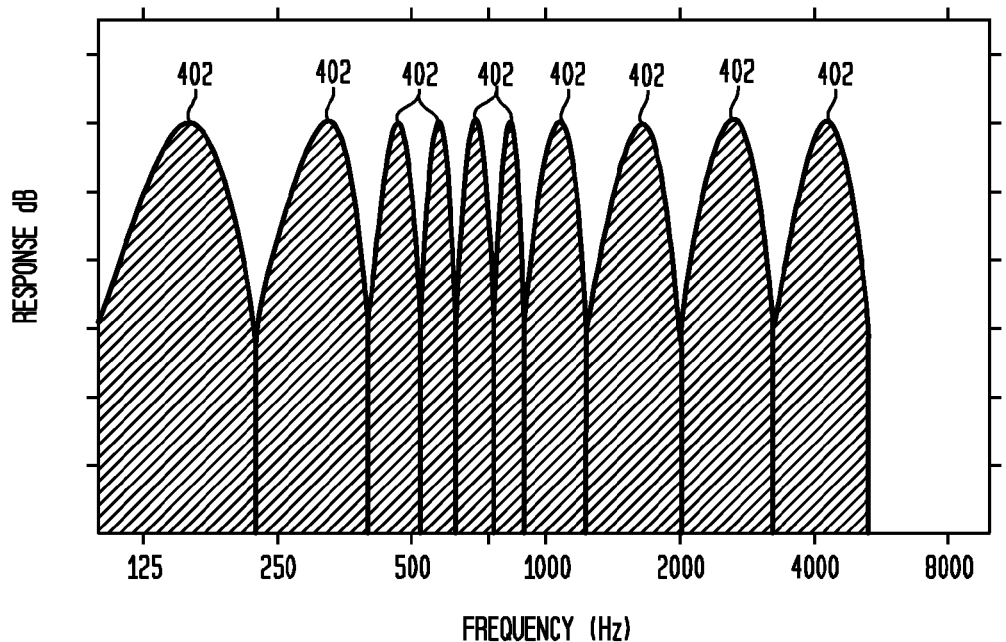
FIG. 4 illustrates one exemplary set of frequency bands for application of acoustic stimulation in a bimodal hearing prosthesis, in accordance with an embodiment of the present invention.

In filtering the signal, preprocessor 302 may obtain a plurality of signal components corresponding to frequency bands for application of acoustic stimulation. FIG. 4 illustrates one exemplary set of frequency bands for application of acoustic stimulation. Pre-processor 302 may band-pass filter the signal received from microphone 124 to obtain 10 different signals for the 10 frequency bands 402 of the illustrated embodiment.

Figure 5:
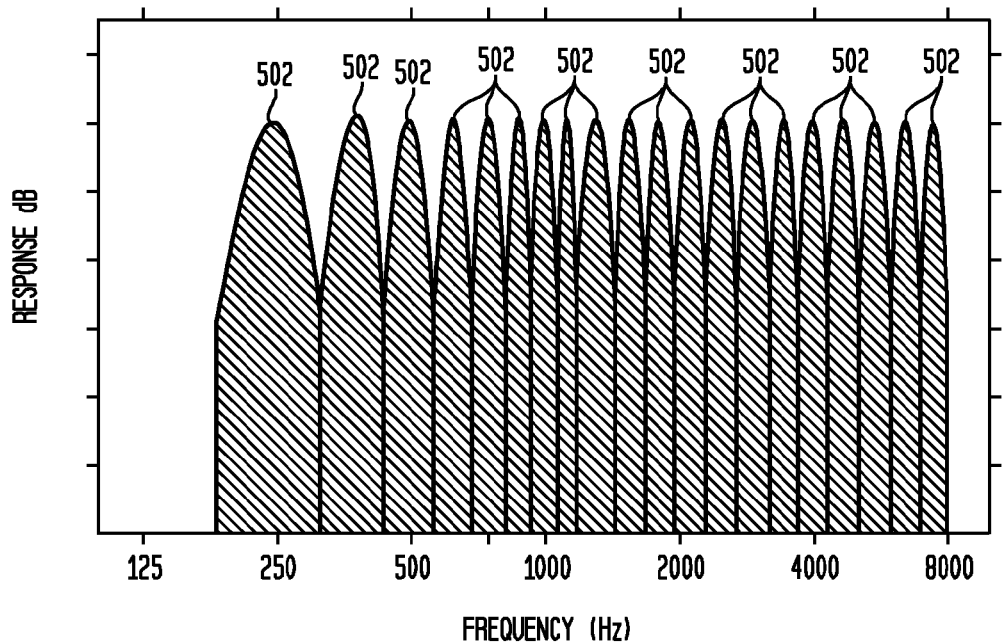
FIG. 5 illustrates one exemplary set of frequency bands for application of electric stimulation in a bimodal hearing prosthesis, in accordance with an embodiment of the present invention.

Preprocessor 302 may additionally also obtain a plurality of signal components corresponding to frequency bands for application of electrical (and/or acoustic) stimulation. FIG. 5 illustrates one exemplary set of frequency bands for application of electric stimulation. Pre-processor 302 may also band-pass filter the signal received from microphone 124 to obtain 20 different signals for the 20 frequency bands 502 of the illustrated embodiment. Pre-processor 302 may use, for example, one or more Fast Four Transforms (FFT) or one or more banks of band-pass filters in obtaining the signal components for acoustic and electrical stimulation.

As noted above, sound processor 126 may use a MAP specifying parameters for use by a sound processor in providing stimulation to the recipient. This MAP may be stored in a memory of sound processor 126 and accessed by the various functional blocks of sound processor 126. This MAP may comprise one or more parameters specifying one or more cut-off frequencies for the frequency sub-bands for the electrical and acoustic stimulation. In operation, preprocessor 302 may access and use this MAP to obtain the cut-off frequency(s) in determining the signal components to send to electrical signal analyzer 304 and acoustic signal analyzer 306.

Figure 6:
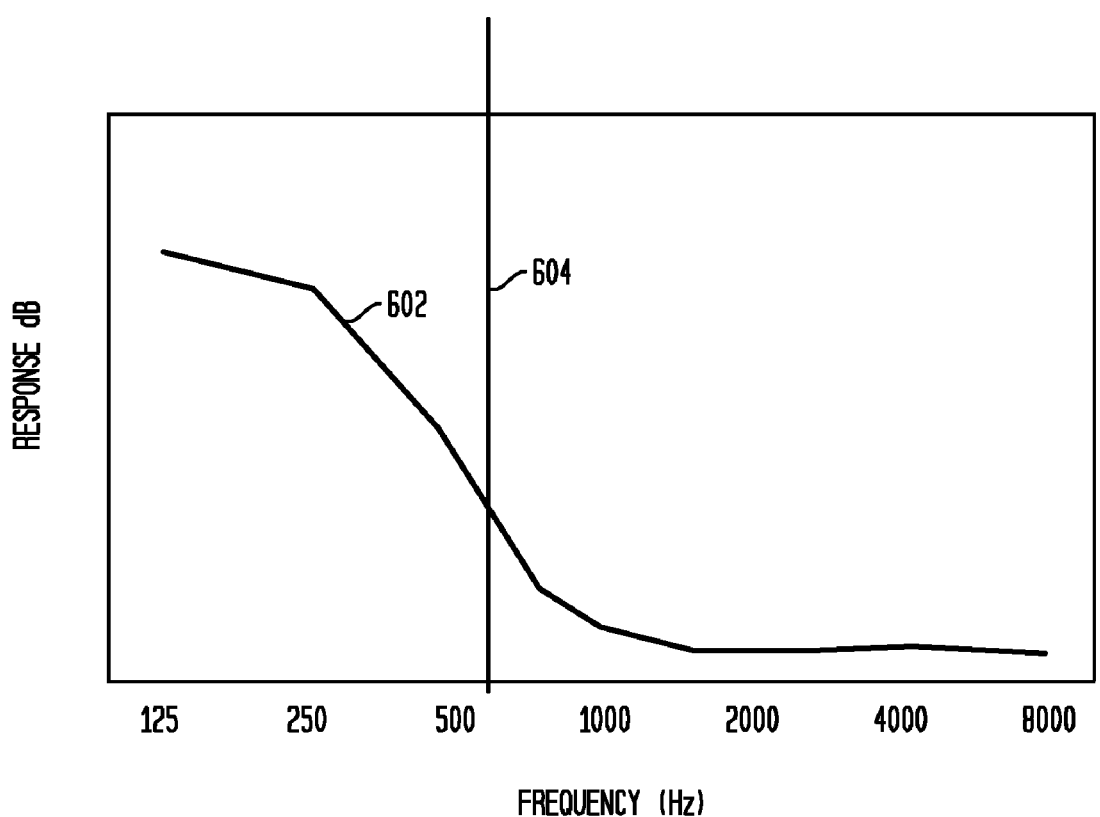
FIG. 6 illustrates an audiogram of a recipient experiencing hearing loss at higher frequencies to illustrate the concept of a cut-off frequency, in accordance with an embodiment of the present invention.

FIG. 6 illustrates an audiogram of a recipient experiencing hearing loss at higher frequencies to illustrate the concept of a cut-off frequency. As illustrated, by curve 602 the recipient has minor hearing loss at low frequencies, while natural hearing is severely diminished at higher frequencies. Line 604 represents the point at which curve 602 falls below a level where the recipient may experience natural hearing with the aid of a hearing aid.

Figure 7:
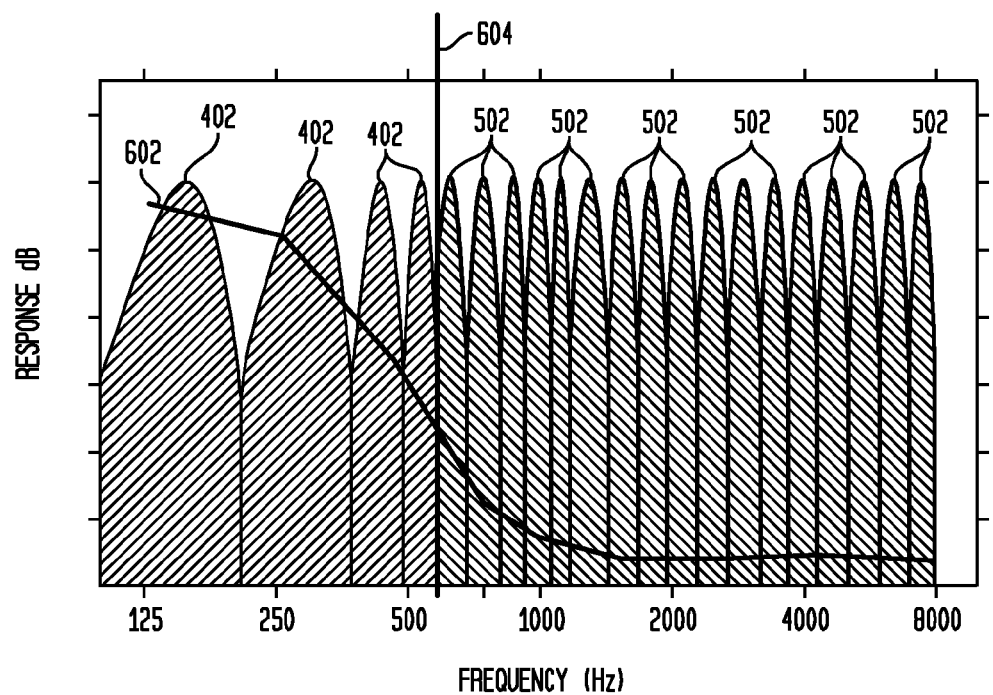
FIG. 7 is a conceptual diagram illustrating frequency bands for application of acoustic and electrical stimulation using a single cut-off frequency, in accordance with an embodiment of the present invention.

FIG. 7 illustrates a conceptual diagram illustrating frequency bands for application of acoustic and electrical stimulation using a single cut-off frequency, in accordance with an embodiment of the present invention. As illustrated, acoustic stimulation is applied for frequency bands 402 falling below cutoff frequency 604 and electrical stimulation is applied for frequency bands 502 above cutoff frequency 604.

Figure 8:
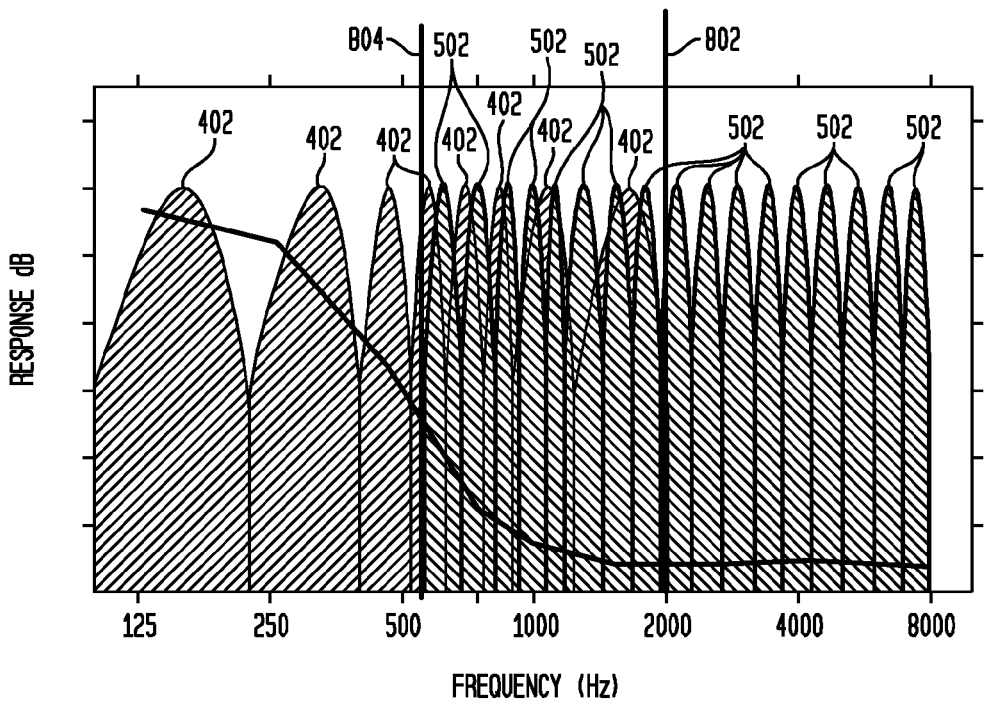
FIG. 8 is a conceptual diagram illustrating frequency bands for application of acoustic and electrical stimulation using multiple cut-off frequencies, in accordance with an embodiment of the present invention.

FIG. 8 illustrates a conceptual diagram illustrating frequency bands for application of acoustic and electrical stimulation using multiple cut-off frequencies, in accordance with an embodiment of the present invention. As illustrated, acoustic stimulation is applied for acoustic frequency bands 402 falling below an acoustic cut off frequency 802; and, electrical stimulation is applied for frequencies above an electric cut off frequency 804.

It should be noted that the above described examples of cutoff frequencies are provided for illustrative purposes to demonstrate how a cutoff frequency(s) may be used in a MAP to specify the frequency range (e.g., the frequency sub-bands) for application of acoustic stimulation and the frequency range for application of electrical stimulation. In operation, preprocessor 302 may use these parameter(s) in the MAP to determine which signal components to select and transfer to the electric signal analyzer 304 and acoustic signal analyzer 306, respectively.

Electric signal analyzer 304 processes the received signal components to determine the stimulation signals for application via stimulating lead assembly 118. Electrical signal analyzer 304 may function in a manner similar to a sound processor of a conventional cochlear implant configured to solely provide electrical stimulation. Acoustic signal analyzer 306 determines the signal for driving loudspeaker 158 in providing acoustic stimulation to the recipient. Acoustic signal analyzer 306 may function in a manner similar to a sound processor for a conventional hearing aid configured to solely provide acoustic stimulation.

In accordance with certain embodiments of the present invention, acoustic signal analyzer 306 and electrical signal analyzer 304 comprise respective delay circuits, respectively, for delaying one or both of the electrical signals to ensure substantially simultaneous stimulation of the cochlea by loudspeaker 158 and stimulating lead assembly 118. Such delay circuits may be any type of delay circuits now or later developed, and may be implemented in hardware, software or any combination thereof. Substantial simultaneous stimulation of the cochlea is desirable so that the implant recipient does not perceive a delay between the two types of stimulations. Such a delay could be bothersome to the implant recipient and interfere with the enjoyment and/or effectiveness of the recipient's hearing. In an embodiment, sound processor 126 may implement a mechanism such as described in U.S. patent application Ser. No. 11/434,929 entitled "Simultaneous Delivery of Electrical and Acoustical Stimulation in a Hearing Prosthesis."

It should be noted that FIG. 3 is a simplified functional block diagram provided for explanatory purposes. In actual implementations, the bimodal cochlear implant may include various other components along both the electrical signal delivery path and acoustic signal delivery path, such as, for example, equalizers, etc. Further, the functional blocks of the sound processor of FIG. 3 may be implemented in hardware, software, or a combination of same.

Figure 9:
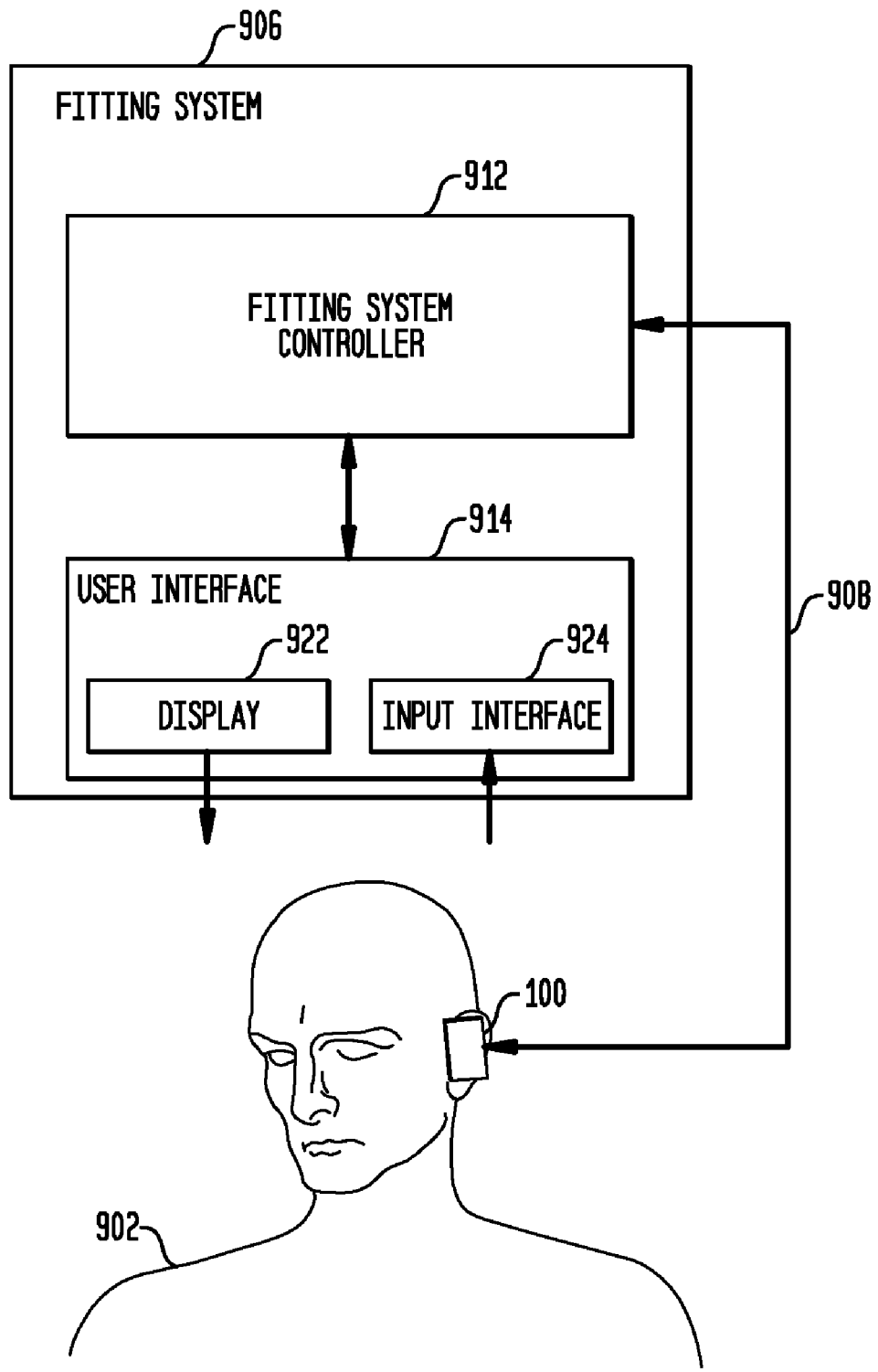
FIG. 9 is a schematic diagram illustrating one exemplary arrangement in which a recipient operated fitting system may be used in fitting a bimodal stimulating medical devices, in accordance with an embodiment of the present invention.

FIG. 9 is a schematic diagram illustrating one exemplary arrangement 900 in which a recipient 902 operated fitting system 906 may be used in fitting a bimodal stimulating medical devices, in accordance with an embodiment. As illustrated, a recipient 902 has a bimodal cochlear implant system 100 attached to one ear. It should, however, be understood that in other embodiments, fitting system 906 may be used in fitting a bi-lateral system to a recipient. A bi-lateral system refers to a system in which a hearing device (e.g., a single or multi-mode cochlear implant system) to both ears of the recipient. For example, fitting system 906 may be used in fitting alternative devices to a recipient to be fitted with a bi-lateral hearing system, such as, for example, in which a bone conduction device is fitted to each of the recipient's ears, a cochlear implant is fitted to each ear, a middle ear mechanical stimulation device is fitted to one or both ears, an inner ear mechanical stimulation device is fitted to one or both ears, etc.

In the embodiment illustrated in FIG. 9, sound processor 126 of cochlear implant 100 may be connected directly to fitting system 906 to establish a data communication link 908 between the sound processor 126 and fitting system 906. Fitting system 906 is thereafter bi-directionally coupled by means of data communication link 908 with sound processor 126. It should be appreciated that although sound processor 126 and fitting system 906 are connected via a cable in FIG. 9, any communications link now or later developed may be utilized to communicably couple the implant and fitting system.

Fitting system 906 may comprise a fitting system controller 912 as well as a user interface 914. Controller 912 may be any type of device capable of executing instructions such as, for example, a general or special purpose computer, digital electronic circuitry, integrated circuitry, specially designed ASICs (application specific integrated circuits), firmware, software, and/or combinations thereof. User interface 914 may comprise a display 922 and an input interface 924. Display 922 may be, for example, any type of display device, such as, for example, those commonly used with computer systems. Input interface 924 may be any type of interface capable of receiving information from a recipient 902, such as, for example, a computer keyboard, mouse, voice-responsive software, touch-screen (e.g., integrated with display 922), retinal control, joystick, and any other data entry or data presentation formats now or later developed.

Figure 10:
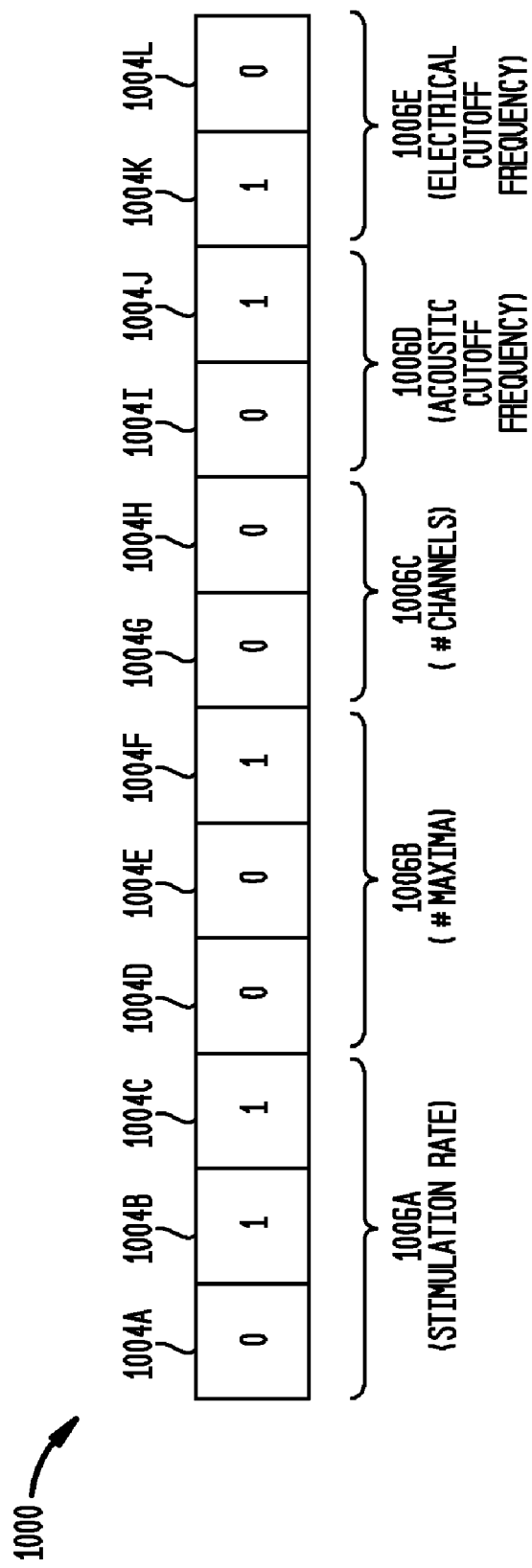
FIG. 10 illustrates an exemplary MAP comprising a set of 8 binary genes, in accordance with an embodiment of the present invention.

Fitting system 906 may be configured to perform a MAP search using a genetic algorithm. In performing the genetic algorithm search, fitting system 906 may represent the MAPs using a bit string comprising a set of $N_b$ 'genes' (bits), wherein the number of possible unique MAPs is $2^{Nb}$. FIG. 10 illustrates an exemplary MAP 1000 comprising a set of 8 binary genes 304A-304H ($N_b$=8). Each of the 8 bits 1004 may be used to individually or collectively designate several parameters for cochlear implant system 100.

In the example shown in FIG. 10, five such parameters 1006A-1006E are designated. Three bits 1004A-1004C are used to select a parameter 1006A of stimulus rate (the rate, in Hz, at which high-energy channels are selected and stimulus pulses are delivered to groups of N electrodes), three bits 1004D-1004F are used to select a parameter 1006B of spectral maxima counts (the number N of electrodes periodically selected to be stimulated, representing the N frequency bands with the highest energy at the time), and two bits 1004G-1004H select a parameter 1006C of the quantity of channels or frequency bands, used to represent the sound spectrum. Each of these first three parameters 1006A-1006C are for use in application of electrical stimulation. Additionally, as illustrated bits 1004I-1004J specify a parameter 1006G for the acoustic cutoff frequency and bits 1004K-1004L select a parameter 1006I for the electrical cutoff frequency. Other parameters are assumed to be constant or derived from one of the three represented parameters 1006.

It should be understood that FIG. 10 is exemplary only and provided to illustrate how a bit string may be used to represent various parameters of a MAP; and, in other embodiments the number of bits and what they represent may be different in alternative embodiments. For example, rather than simply using two bits to represent each cutoff frequency, in other embodiments a greater number of bits may be used. Or, for example, rather than including two separate cutoff frequency parameters, in an embodiment a single cutoff frequency parameter may be used such as discussed above with reference to FIG. 7.

Figure 11:
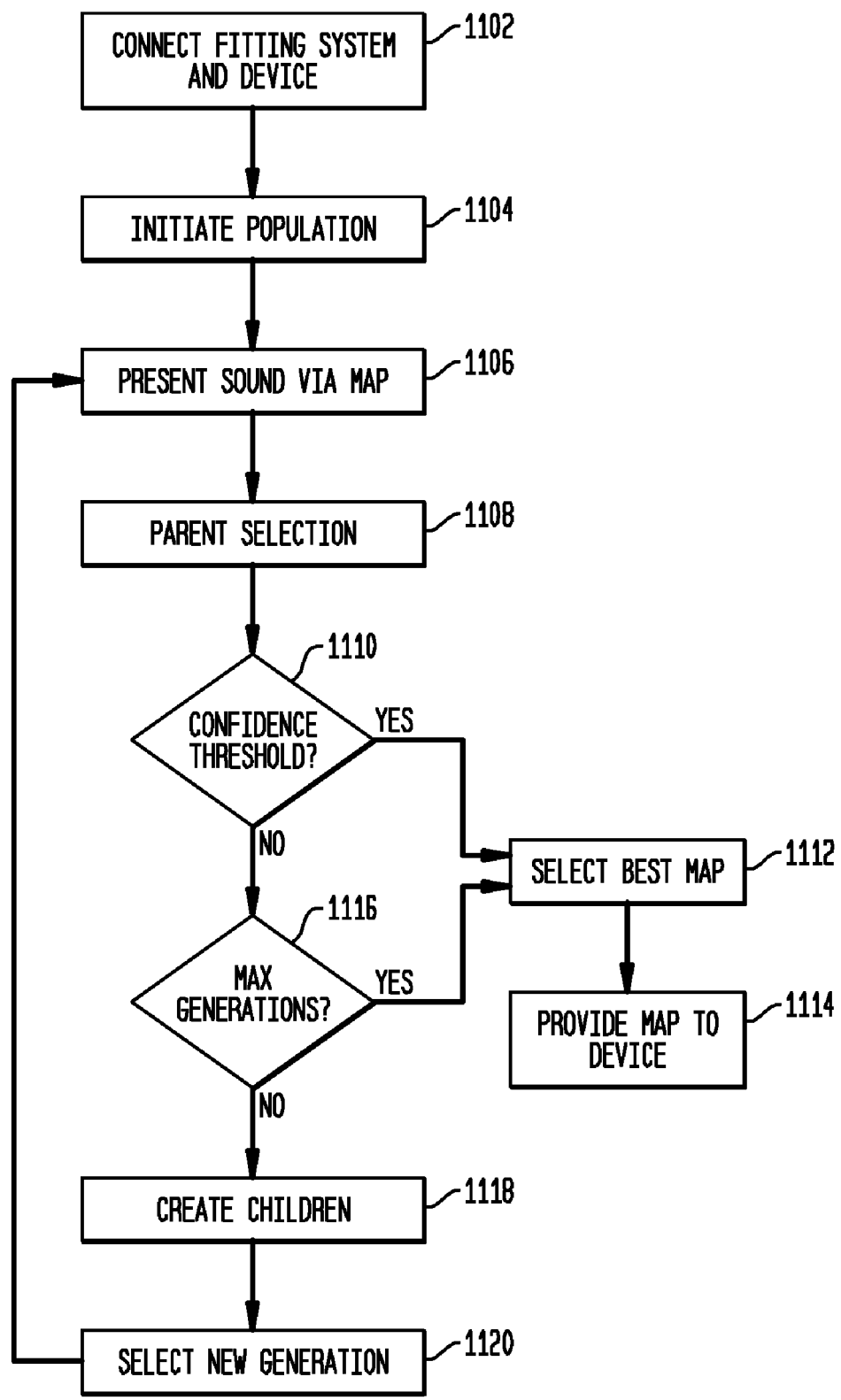
FIG. 11 is a high-level flow chart of an exemplary method for determining a MAP using a genetic algorithm, in accordance with an embodiment of the present invention.

FIG. 11 is a high-level flow chart of an exemplary method for determining a MAP using a genetic algorithm, in accordance with an embodiment. FIG. 11 will be discussed with reference to the fitting system illustrated in FIG. 9.

A recipient 902 may initiate the process by connecting cochlear implant system 100 to fitting system 906 at block 1102. This may be accomplished by plugging a cable into the speech processor 126 of the cochlear implant system 100 and the fitting system 206. Or, for example, fitting system 906 may connect wirelessly to bone conduction device 901 and/or cochlear implant system 100 in response to, for example, the recipient entering an instruction via user interface 914 that instructs fitting system 906 to wirelessly initiate a connection with cochlear implant system 100. This connection may also cause the fitting system to begin some initialization procedures. These initialization procedures may include a calibration step to help ensure that if the fitting system 906 delivers a sound signal to the recipient 902 via a speaker at a specified loudness, the sound may be delivered with a constant sound level pressure to the sound processor 126 of the cochlear implant system 100 by the fitting system 906.

The fitting system 906 may generate an initial population of MAPs at block 1104. In an embodiment, the initial population may comprise 8 selected MAPs. It should be noted that this number need not be 8, but may vary depending on the implementation. Various techniques may be used to select this initial generation of MAPs. For example, this selection may be performed by selecting at random from among the set of possible MAPs. Or, for example, in order to insure greater diversity among the selected initial generation of MAPs, the MAPs may be selected so that the each parameter value is represented in at least one MAP. For parameters in which the number of possible variables is greater than the number of MAPs in the initial generation, the values may be randomly selected such that each MAP in the initial generation has a unique value for the parameter. For example, if there are 12 possible parameter values, a first one of the parameter values may be randomly selected from among the 12 possible values, and then when selecting the parameter value for the second MAP the fitting system selects from amongst the 11 remaining unselected values, and so on.

Or, for example, in an embodiment, in order to insure that this initial MAP set has a sufficient measure of heterogeneity, its diversity may be computed. In one embodiment, diversity is defined as the average Hamming distance between the various MAPs, and it ranges between 0 and 1, with 1 indicating maximum diversity and 0 indicating minimum diversity. If the diversity is below a threshold, for example, 0.53, then the initial generation has an insufficient diversity, and the fitting system 906 may select a new set of MAPs. Moreover, pre-selected MAPs may also be included among the MAPs of the first generation. These pre-selected MAPs may be drawn, for example, from prior runs of the fitting procedure, MAPs stored in a memory of fitting system 906, or MAPs selected by a clinician based on his experience, suggestions and recommendations from others, etc. This initial population of MAPs may be referred to as the first generation of MAPs.

At block 1106, the population of MAPs are presented to the recipient. This may involve fitting system 906 sequentially providing each MAP to the recipient's cochlear implant system 100 and then presenting an audible signal that that is processed by the provided MAP. For example, if fitting system 906 uses a MAP such as MAP 1000 of FIG. 10, fitting system 906 may provide the parameter values for the parameters 1006A-1006E to cochlear implant system 100. Sound processor 126 (e.g. a control functional block of sound processor 126) may then provide parameters 1006A-1006C to electric signal analyzer 304 and provide the cutoff frequency parameter values for parameters 1006D and 1006E to pre-processor 302. In providing these parameter values, fitting system 206 may provide the bits from the MAP or alternatively may provide the actual parameter values. For example, fitting system 906 may store a look up table for looking up a parameter corresponding to a particular bit patter. As an example, if the MAP contains a parameter for a gain curve (e.g., for amplification of the signal by acoustic signal analyzer 306), the gain curve shapes for a particular bit pattern may be stored in a look up table. Fitting system 906 may then look up the shape corresponding to the specified bits in a MAP to determine the gain curve to be provided to acoustic signal analyzer 306.

The audible signal may be a sound token that comprises any type of sound, such as a single speaker reading aloud from a newspaper or a passage from an audio book, a particular piece of music, or portion of same, a musical instrument, a car horn, etc. The audible signals (e.g., sound tokens) may be stored in a file contained in a library of audible signals that is stored, for example, in fitting system 906 or in an external storage device connected to fitting system 906.

In an embodiment, fitting system 906 may randomly select a sound token for each of the 8 MAPs. Fitting system 906 may then download the MAP corresponding a particular sound token to the cochlear implant system 100, and then play the audible signal (e.g., the sound token). This audible signal may be played using, for example, one or more speakers connected to fitting system 906, such as, for example, a set of headphones worn by the recipient 902. Further, recipient 202 and fitting system 202 may be located in a room such as, for example, a sound proof room, designed to minimize external noise interfering with the presentation of the audible signal. Or, for example, fitting system 906 may provide the audible signal directly to cochlear implant system 100 via data communications link 908. After fitting system 906 presents the first sound token to the recipient 902, the fitting system 906 may download the parameter values for the next MAP to the cochlear implant system 100 and then play the corresponding sound token to the recipient 902. This process may then continue sequentially until fitting system 906 presents all 8 MAPs to the recipient 902.

After fitting system 906 presents each of the sound tokens and corresponding MAPs to the recipient 902, fitting system 906 may then receive an indication from the recipient 902 regarding which sound tokens were perceived as good by the recipient 902. Using this indication, fitting system 906 may determine the parents for the next generation of MAPs at block 1108. In an embodiment, all MAPs identified as good by the recipient may be selected as parent MAPs for generating the next generation of MAPs. Or, for example, the recipient 902 may select the 4 MAPs that the recipient considered to be the best MAPs and these 4 best MAPs are selected as the parent MAPs.

In yet another embodiment, the recipient may be presented with a sound token comprising a statement, and the recipient asked to identify what they heard. Then, if the recipient 202 correctly identified what they heard, the corresponding MAP may be used as a parent MAP generating the next generation of MAPs. A further description of user interface that may be used to perform such an objective test in identifying good MAPs is presented below with reference to FIG. 14.

It should be noted that these are but some exemplary mechanisms that may be used at blocks 1106 and 1108 for selecting parent MAPs from the population of MAPs, and other mechanisms may be used without departing from the present invention. For example, mechanisms for selecting parent MAPs may be used such as described in U.S. patent application Ser. No. 12/557,208, entitled "Using a Genetic Algorithm to Fit a Cochlear Implant System to a Recipient," the entire contents of which are hereby incorporated by reference.

Further, it should be noted that although blocks 1106 and 1108 are illustrated as separate blocks, this was done for illustrated purposes, and in embodiments they may be combined or involve an iterative process where the two blocks are repeated until a certain condition occurs, such as all MAPs are presented or a particular number of MAPs are selected.

Fitting system 906 may then check to see if a diversity threshold has been reached at block 1110 for the selected MAPs. In an embodiment, fitting system 906 may determine that the diversity threshold has been reached if the value of each bit of the MAP bit string is considered to have converged and its value is known with a particular confidence level based on the historical distribution of that bit. For instance, bit #1 may be considered converged if it has historically either been a "1" or a "0" a particular percentage of the time (e.g., 95% of the time according to a binomial distribution) over its entire history. As such, probability dictates that there is a 95% chance that this bit will be the same value again in a subsequent generation. When all bits reach this confidence level (e.g., 95%), fitting system 206 may determine that the diversity threshold has been met. In other words, in this example, in this example, fitting system 206 determines that the diversity threshold has been met if the confidence level for each of the bits exceeds the specified confidence level (e.g., 95%).

Because the early generations of a genetic algorithm search include MAPs that are deliberately random, an embodiment may analyze a multitude of historical sequences of generations from every possible initial generation through the current/latest generation. Computing confidence levels using, in an embodiment, every possible historical sequence of generations may help expedite the convergence of the algorithm. Computing confidence levels excluding these initial deliberately random generations may help expedite the convergence of the algorithm. An exemplary mechanism for such an expedite convergence algorithm is provided in U.S. patent application Ser. No. 12/557,233, entitled "Using a Genetic Algorithm Employing an Expedited Convergence Algorithm," the entire contents of which are hereby incorporated by reference.

If at block 1110 the diversity threshold has not been achieved, fitting system 906 may determine if the maximum number of generations has been reached at block 1116. If so, fitting system 906 may proceed to block 1110 to select the final MAP. Otherwise the algorithm continues to block 1118.

Fitting system 906 may determine if the maximum number of generations has been reached by maintaining a tally of each pass through block 1116 and then comparing this tally against a particular value specifying the maximum number of generations to be used in determining the final MAP. For example, in an embodiment, fitting system 906 may set a generation number variable, G, equal to one (G=1) at block 1104, and then increase G by 1 (G=G+1) at block 1118 or 1120. It should be noted that this is but one mechanism in which fitting system 906 may maintain a generation number variable G that is equal to the current generation number of the genetic algorithm search, and other mechanisms may be employed.

Fitting system may then generate child MAPs at block 1118. Various techniques may be used for generating the child MAPs. For example, in an embodiment, a child MAP may be generated by pairing two of the parent MAPs selected at block, selecting a cut point, and then generating two children MAPs from the selected parents. In an embodiment, the genes for a child MAP to the left of the cut point may come from one parent, and the genes to the right of the cut point may come from the other parent.

Figure 12:
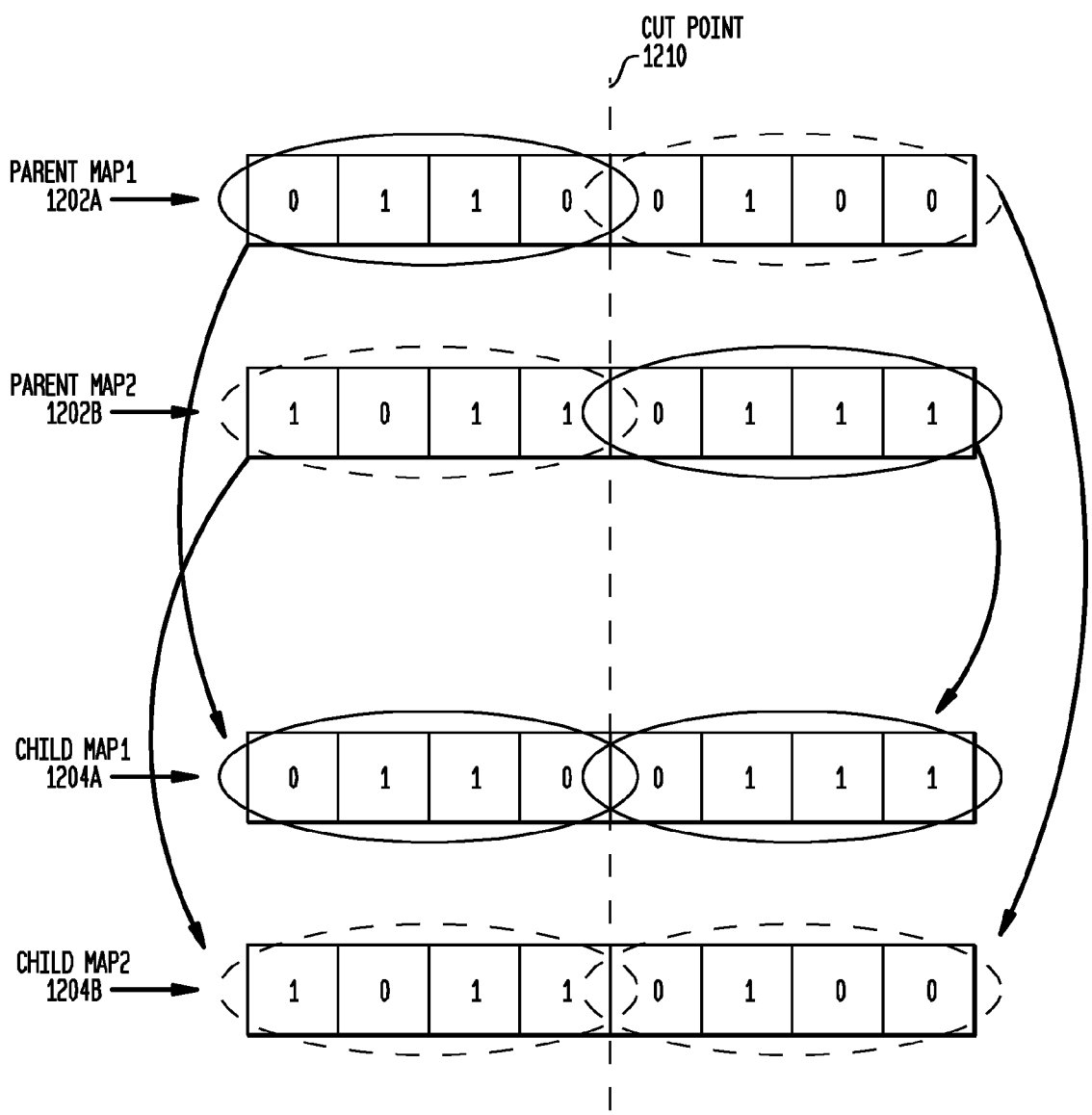
FIG. 12 illustrates one example of how an offspring MAP may inherit genes from each parent MAP, in accordance with an embodiment of the present invention.

FIG. 12 illustrates one example of how an offspring MAP may inherit genes from each parent MAP, in accordance with an embodiment. In the illustrated example, each parent MAP 1202A and 1202B is represented by an 8 bit string. Fitting system 906 may select a cut point 1210 for the bit string of each parent MAP 1202A and 1202B. The selected cut point 1210 may be between any particular bits of the bit strings, and in FIG. 12 the cut point 1210 is selected in the middle of each bit string. Further, in the illustrative example, the cut point is allowed to vary randomly across pairings. For example, in an embodiment, the fitting system 906 may analyze the two parent MAPs to identify bits that are different between the parents, and then randomly select a cut point between the bits identified to be different. Alternatively, the cut points can be made in the same position for all the pairings.

Then, fitting system 906 may generate two child MAPs 1204A and 1204B from the parent MAPs 1202, where the first child MAP 1204A includes bits of parent MAP 1202A to the left of the cut point 1210 (i.e., the first 4 bits) and the of the parent MAP 1202B to the right of the cut point 1210 (i.e., the last 4 bits). Similarly, the genes of the second child MAP 1204B include the first 4 bits of parent MAP 1202B and the last 4 bits of parent MAP 1202A. It should be noted that this is but one example of how child MAPs may be generated from parent MAPs, and other mechanisms may be used.

Fitting system 906 may then select at block 1120 the child MAPs for the next generation of MAPs to be presented to the recipient. Various techniques may be used for selecting the new generation of MAPs, such as those discussed in the above-referenced U.S. patent application Ser. No. 12/557,208, entitled "Using a Genetic Algorithm to Fit a Cochlear Implant System to a Recipient." For example, if fitting system 906 generates an overloaded generation at block 1116, fitting system 906 may randomly select at block 1118 a particular number (e.g., 8) of MAPs from this pool of child MAPs. Then, fitting system 906 may use these 8 randomly selected MAPs as the MAPs for the next generation presented to the recipient 902 at block 1106

Fitting system 906 may then return to block 1106 and present audible signals processed by this next generation of MAPs to the recipient. The process may then continue until either the confidence threshold is exceeded at block 1110 or the maximum number of generations is reached at block 1114.

Once the confidence threshold or maximum number of generations has been reached, fitting system 906 may then determine, at block 1112, the particular MAP to be used by the cochlear implant 100. Various techniques may be used for determining the final MAP depending, for example, on how the process was terminated. For example, if the confidence threshold was reached by a determination that each bit of the MAP is known with a confidence level exceeding the specified confidence level (e.g., 95%), then fitting system 906 may simply use these known bit values for the final MAP. The term final MAP is used in this description to refer to the MAP that is determined by the genetic algorithm and subsequently downloaded to the cochlear implant 100 for use after fitting the implant. However, it should be noted that this MAP may be changed after fitting, such as, for example, by the recipient 902 re-fitting the cochlear implant 100 at a later time.

If, however, block 1106 is reached due to, for example, the maximum number of generations being reached or a determination that the confidence threshold was exceeded by some other mechanism, fitting system 906 may use various other mechanisms for determining the final MAP. For example, fitting system 906 may present audible signals processed by each of the final selected MAPs to the recipient 902 and receive an indication from the recipient regarding which MAP is considered the best MAP. Or, for example, fitting system 906 during the process may store an indication regarding each MAP that is selected at block 1108 through each iteration, then fitting system 906 may select the MAP that was selected by the recipient 902 the most number of times at block 1108 and use this MAP as the final MAP.

Or, in yet another example, fitting system 906 may select a number (e.g., 4) of MAPs that were selected by the recipient 902 at block 1108 the most number of times and present audible signals processed by these selected MAPs (referred to as the final round) to the recipient 902. In presenting audible signals processed by the final round of MAPs to the recipient, fitting system 906 may provide multiple rounds of presentations, where each MAP is presented to the recipient 902 in each round using a different sound token. The recipient 902 may then select the "best" MAP for each round, and then after a particular number of rounds (e.g., 4 rounds), the MAP that was selected as best the most amount of times is determined to be the final MAP. If after 4 rounds, there is a tie, a series of one or more rounds may be run for the top tied MAPs to determine the final MAP.

After the final MAP is determined at block 1112, fitting system may download this determined MAP to cochlear implant 100 for subsequent use at block 1114. In addition, fitting system 906 may store this final MAP along with information identifying the recipient 202 and/or cochlear implant 100 in a storage of fitting system 906. Thus, in the event the recipient's cochlear implant 100 becomes corrupted, fitting system 100 may be able to more quickly re-provide the determined MAP to cochlear implant. Or, for example, if the genetic algorithm search is repeated for the recipient at a later date, an audiologist may be able to view and compare the newly determined MAPs as well as previously determined MAPs for the recipient, or even use the previously determined MAP(s) as one of the MAP in the initial generation of the genetic algorithm search.

After the final MAP is determined at block 1112, fitting system may download the parameters values for this determined MAP to cochlear implant system 100 for subsequent use at block 1114. In addition, fitting system 906 may store this final MAP along with information identifying the recipient 902, cochlear implant system 100, in a storage of fitting system 906. Thus, in the event the recipient's cochlear implant system 100 becomes corrupted; fitting system 100 may be able to more quickly re-provide the determined MAP to cochlear implant and bone conduction device. Or, for example, if the genetic algorithm search is repeated for the recipient at a later date, an audiologist may be able to view and compare the newly determined MAPs as well as previously determined MAPs for the recipient, or even use the previously determined MAP(s) as one of the MAP in the initial generation of the genetic algorithm search.

Figure 13:
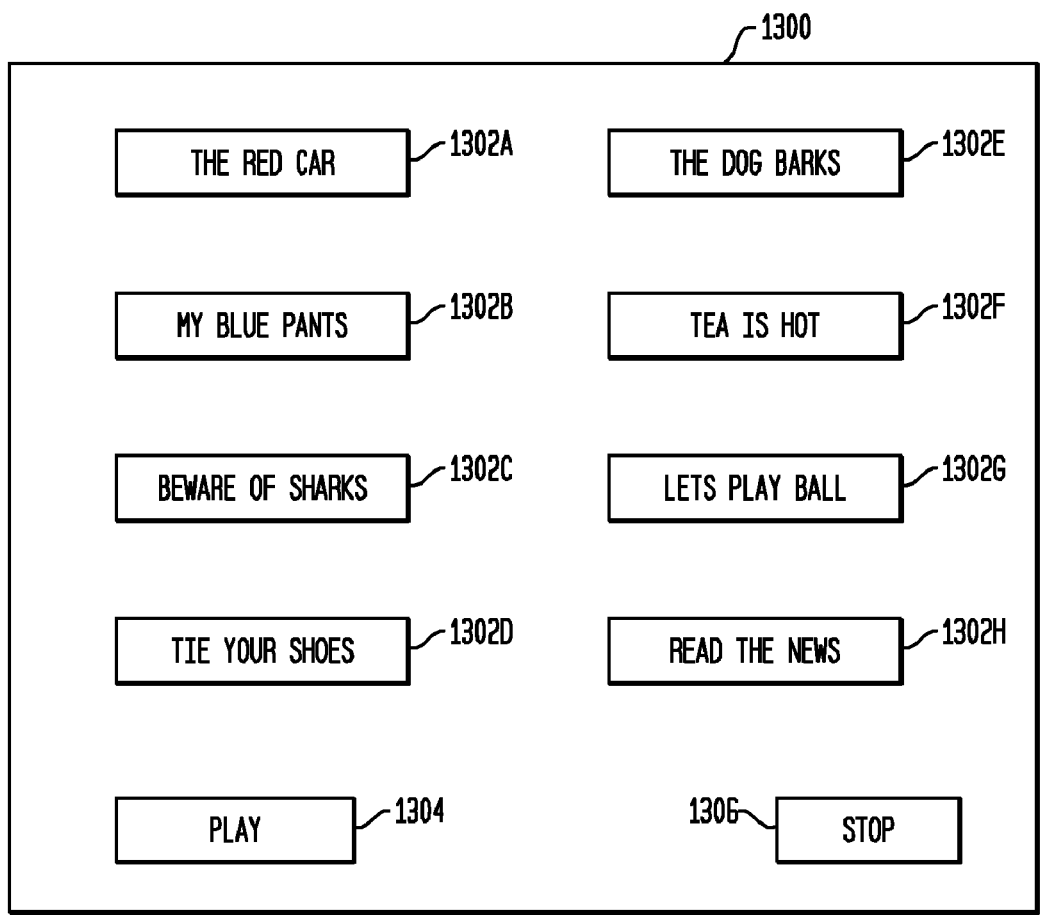
FIG. 13 illustrates an exemplary GUI that may be provided to a recipient for obtaining the recipients perception of applied stimulation, in accordance with an embodiment of the present invention.

FIG. 13 illustrates an exemplary GUI 1300 that may be provided to a recipient for obtaining the recipients perception of applied stimulation, in accordance with an embodiment. As illustrated, GUI 1300 may comprise a set of icons 1302 that the recipient may select to indicate which phrase they believe they heard. For example, these icons 1302 may include an icon for selecting that the recipient heard any one of eight phrases 1302A-H. This GUI 1300 may be displayed on display 922. The recipient may, using input interface 924, select the icon 1302 corresponding to the phrase they believe they heard. The input interface 224 may then provide this response to fitting system controller 912.

Additionally, GUI 1300 may include a play icon 1304 that the recipient may select to direct the fitting system controller 912 to play the phrase that the recipient 902 is to identify. The GUI 1300 may also comprise a stop button 1306 that the recipient 902 may select to stop the process, such as if the recipient needs to leave for any purpose.

It should be noted that GUI 1300 is exemplary only and provided to illustrate one example of a GUI interface that may be used for determining whether a recipient can correctly identify a sound token processed by a particular MAP. For example, in other embodiments, the sound token may be a sound from a musical instrument and the icons that the recipient may select may be in the shape of different instruments and/or be identified by the name of a particular instrument. Further, in other embodiments, the recipient 902 may be able to use check boxes, pull-downs, or other mechanisms for identifying a particular sound.

In an embodiment in which the recipient 902 is asked to correctly identify a particular sound, the fitting system 1306 may sequentially present a predetermined number of MAPs (e.g., 8) to the recipient each processing a different sound token. Then, the MAPs corresponding to sounds that the recipient correctly identified are deemed by the fitting system 906 as good and accordingly selected at block 1108. As such, in this example, the number of MAPs selected at block 1108 may vary between 0 and all of the presented MAPs. In the event no MAPs are selected at block 1108, the process may return to block 1106 and the previously set of MAPs may be re-presented to the recipient 902, although this time with a new set of sound tokens. If, however, no MAPs are again selected at block 1108, the process may be re-started and returned to block 1104.

In yet another embodiment, the steps of blocks 1106 and 1108 may be repeated until the recipient correctly identifies a particular number of sound tokens. Then, fitting system 906 may select as parents the MAPs corresponding to the correctly identified sound tokens. For example, in an embodiment, fitting system 1118 may randomly select a child MAP from the child MAPs generated at block 1118 and then present the selected MAP to the recipient 902. The fitting system 902 may then ask the recipient 902 to correctly identify a sound token processed using the MAP. After which, fitting system 906 may randomly select another child MAP and present this MAP to the recipient. This process may then continue until the recipient correctly identifies a particular number of sound tokens (e.g., 4). The fitting system 906 may then use the MAPs corresponding to the correctly identified sound tokens as the parent MAPs selected at block 1108.

In certain embodiments, certain sound tokens may work better with other MAPs or certain sound tokens may be simply difficult for the recipient to understand regardless of the MAP used to process the sound token. For example, if a sound token comprises speech from a person with a strong southern accent, but the recipient 202 speaks with a strong English accent, the sound token may be difficult for the recipient to identify regardless of the MAP. Thus, it is possible that good MAPs may not be selected at block 1108 if they are paired with a bad sound token. In order to mitigate the impact of bad sound tokens, in an embodiment, blocks 1106 and 1108 may be repeated two or more times. For example, in a first pass through blocks 1106 and 1108, each MAP may be paired with a particular sound token. Then, during the second pass, the same MAPs and sound tokens may be used, but with different sound tokens matched up with different MAPs. For example, in an embodiment, in the second pass, the MAPs considered bad in the first pass may switch sound tokens with the MAPs considered good in the first pass. As an illustrative example, in a first pass MAP "A" processes token "1," "B" processes token "2," "C" processes token "3", "D" processes token "4", "E" processes token "5," "F" processes token "6," "G" processes token "7," and "H," processes token "8." The, if MAPS A, B, C, and D are selected, in the next pass through blocks 1106 and 1108 MAP A may be paired with token 5, B with token 6, C with token 7, D with token 8, E with token 1, F with token 2, G with token 3, and H with token 4. Then, at block 1108, in the second pass through, fitting system 206 may identify any MAP selected in either pass as good and use these MAPs as parents for generating the next generation.

In yet another embodiment, the genetic algorithm may use two or more populations, rather than a single larger population. For example, the genetic algorithm process may be performed two or more times with a different set of MAP parameters for each genetic algorithm search. In one such example, in the first genetic algorithm search, the parameters represented by the MAP may be more critical parameters. Then in the second genetic algorithm search, the parameters determined in the first search will be fixed and the second genetic algorithm search used to identify less critical parameters. For example, in an embodiment, a first genetic algorithm search may be performed using MAPs that specify the stimulation rate, number of electrodes, and number of Maxima to be used. Other parameters may be set to default values during this first search. Then, the parameter values determined during this first genetic algorithm search are fixed, and the second genetic algorithm search may be performed using these previously determined values as fixed terms. The MAP parameters used in the second genetic algorithm may include parameters, such as values for the type of and shape of filters, etc. In other words, the fitting system 206 may sequentially perform multiple genetic algorithm searches where values for different subsets of parameters are identified in each search, and the values identified in previously performed searches are used as fixed values in subsequent genetic algorithm searches.

The above discussed processes, such as FIG. 11, and mechanisms may be embodied on software executable by a computer. Additionally, in an embodiment fitting system 906 may be a recipient's home computer, personal digital assistant (PDA) or other device on which such software is loaded. Additionally, in such an embodiment, a piece of hardware may be used for allowing the recipient's computer to communicate with the recipient's cochlear implant for the purposes of, for example, changing the MAP used by the recipient's cochlear implant. This hardware may be connected to the recipient's computer, PDA, etc. using for example, as USB interface, a firewire interface or any other suitable mechanism. Or, for example, the recipient's computer, PDA, etc. may communicate wirelessly with the recipient's cochlear implant using Wi-Fi, Bluetooth, or any other suitable wireless interface included in the computer and cochlear implant. Additionally, in embodiments, the recipient could perform optimizations at using signals of his or her own choosing (e.g., a spouse's voice, a musical piece, etc.) or simply using the microphone input of the stimulating medical device. In such embodiment, the software may provide the recipient with the ability to upload and store these audible signals for use by the genetic algorithm.

Although the above-discussed embodiments were discussed with a bi-modal cochlear implant configured to provide acoustic and electric stimulation, in other implementations embodiments may be employed in other multi-modal systems. For example, in an embodiment, a genetic algorithm may be employed to obtain a MAP for use in a multi-modal system providing both mechanical and electrical stimulation. In one such system, a bone conduction device (e.g., a Baha) is fitted to one ear of the recipient and a cochlear implant providing electrical stimulation is fitted to the other ear. In such, an embodiment, the MAP may specify parameters for both the bone conduction device and the cochlear implant. A genetic algorithm may then be employed to determine the MAP for use in this mixed mode system. In performing this genetic algorithm search, the bone conduction device and cochlear implant may each be connected to a fitting system such as discussed above with reference to FIG. 9.

In yet another embodiment, a genetic algorithm may be employed by a fitting system to determine a MAP for a multi-modal device providing both mechanical stimulation and electrical stimulation to a single ear of the recipient. The mechanical mode of stimulation provided by the mixed mode cochlear implant system may comprise, for example, direct mechanical stimulation to the recipient's middle ear. In such an embodiment, the cochlear implant system may comprise an electromechanical transducer coupled to the middle ear or inner ear. Any technique now or later developed may be used for coupling the transducer to the inner or middle ear. In an embodiment, the transducer may stimulate the middle ear by direct mechanical coupling via coupling element to ossicles 106 (FIG. 1), such to incus 109 (FIG. 1). One example of an exemplary transducer for providing mechanical stimulation is described in U.S. Pat. No. 5,277,694.

Figure 14:
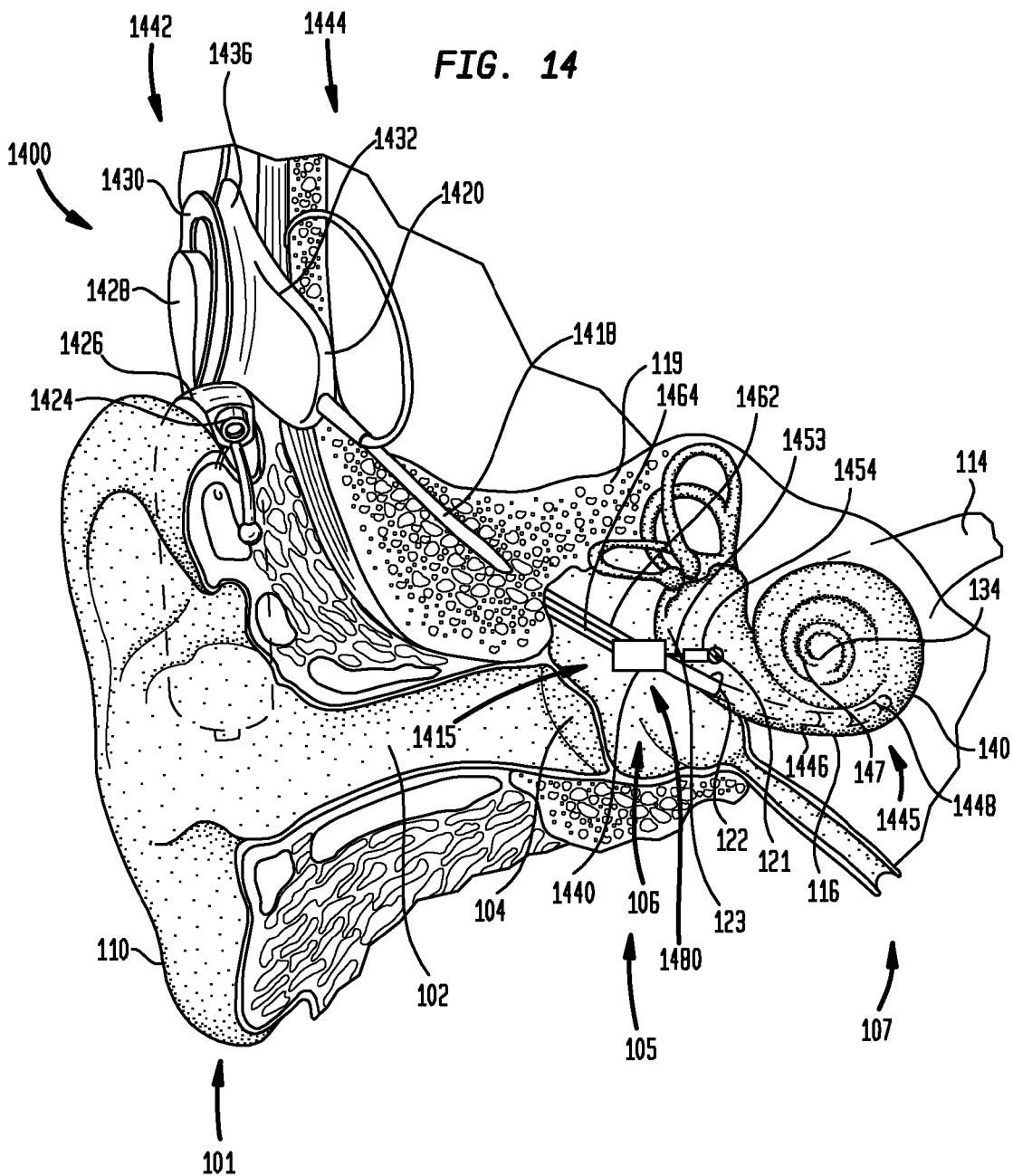
FIG. 14 is a perspective view of bimodal hearing prosthesis configured to provide electrical and mechanical stimulation, in accordance with an embodiment of the present invention.

FIG. 14 is a perspective view of bimodal hearing prosthesis 1400 configured to provide electrical and mechanical stimulation, in accordance with an embodiment of the present invention. Bimodal hearing prosthesis is configured for providing electrical stimulation to cochlea 140 as well as mechanical stimulation to inner ear 107. Bimodal hearing prosthesis 1400 comprises an external component 1442 which is directly or indirectly attached to the body of the recipient, and an internal component 1444 which is temporarily or permanently implanted in the recipient. External component 1442 typically comprises one or more sound input elements, such as microphone 1424 for detecting sound, a sound processor 1426, a power source (not shown), and an external transmitter unit 1428. External transmitter unit 1428 comprises an external coil 1430 and, preferably, a magnet (not shown) secured directly or indirectly to external coil 1430. Sound processor 1426 processes the output of microphone 1424 that is positioned, in the depicted embodiment, by auricle 110 of the recipient. Sound processor 1426 generates encoded signals, sometimes referred to herein as encoded data signals, which are provided to external transmitter unit 1428 via a cable (not shown).

Internal component 1444 comprises an internal receiver unit 1432, a stimulator unit 1420, and a bimodal stimulation system 1480. Bimodal stimulation system 1480 comprises an elongate electrode assembly 1448 and a mechanical stimulation arrangement 1415. Internal receiver unit 1432 comprises an internal coil 1436, and preferably, a magnet (also not shown) fixed relative to the internal coil. Internal receiver unit 1432 and stimulator unit 1420 are hermetically sealed within a biocompatible housing, sometimes collectively referred to as a stimulator/receiver unit.

In the illustrative embodiment of FIG. 14, external coil 1430 transmits electrical signals (i.e., power and stimulation data) to internal coil 1436 via a radio frequency (RF) link. Internal coil 1436 is typically a wire antenna coil comprised of multiple turns of electrically insulated single-strand or multi-strand platinum or gold wire. The electrical insulation of internal coil 1436 is provided by a flexible silicone molding (not shown). In use, implantable receiver unit 1432 may be positioned in a recess of the temporal bone adjacent auricle 110 of the recipient.

As noted, internal component 1444 further includes a bimodal stimulation system 1480. As shown, bimodal stimulation system 1480 comprises an electrode assembly 1448 which is configured to be implanted in cochlea 140. Electrode assembly 1448 comprises a longitudinally aligned and distally extending array 1445 of electrodes 1446, sometimes referred to as electrode array 1445 herein, disposed along a length thereof. Electrode assembly 1448 may be similar to stimulating lead assembly 118 discussed above with reference to FIG. 1.

The proximal end of electrode assembly 1448 is electrically connected to a lead 1462 extending from stimulator unit 1420. In embodiments of the present invention, stimulator unit 1420 generates, based on data signals received at receiver unit 1432, electrical stimulation signals which are delivered to electrode assembly 1448 via lead 1462. The stimulation signals are applied by electrodes 1446 to cochlea 140, thereby stimulating auditory nerve 114.

As shown in FIG. 14, bimodal stimulation system 1480 further comprises mechanical stimulation arrangement 1415. In the illustrative embodiment, ossicles 106 have been omitted from FIG. 14 to illustrate an exemplary location of stimulation arrangement 1415. It should be appreciated that stimulation arrangement 1415 may be implanted without disturbing ossicles 106.

Stimulation arrangement 1415 comprises an actuator 1440 electrically connected to stimulator unit 1420 by lead 1464, a stapes prosthesis 1454 and a coupling element 1453. In this illustrative embodiment, coupling element 1453 connects actuator 1440 to stapes prosthesis 1454 which abuts round window 121. In certain embodiments of the present invention, based on data signals received at receiver unit 1432, stimulator unit 1420 generates actuator drive signals which cause vibration of actuator 1440. This vibration is transferred to the inner ear fluid (perilymph) in the recipient's scala tympani via coupling element 1453 and stapes prosthesis 1454, thereby evoking a hearing percept by the recipient. In an embodiment, bimodal hearing prosthesis 1400 may function in a similar manner to International Application No. PCT/US2009/038937 entitled "A Bimodal Hearing Prosthesis," which is hereby incorporated by reference.

Although the embodiments of FIG. 14 have been described with reference to a bimodal hearing prosthesis 1400 having an external component, it should be appreciated that in alternative embodiments bimodal hearing prosthesis 1400 is a totally implantable device. In such embodiments, sound processor 1426 is implanted in a recipient in the mastoid bone and the sound processor communicates directly with stimulator unit 1420, thereby eliminating the need for transmitter unit 1428 and receiver unit 1432.

Sound processor 1426 may function in a similar manner to sound processor 126 of FIG. 1 with the exception that sound processor 1426 may comprise a mechanical signal analyzer in place of the acoustic signal analyzer 306 (FIG. 3). For example, sound processor 1426 may comprise a storage area in which recipient-specific audiologic adaptation parameters and the audiometry parameters are stored. These parameters may be stored in a MAP that sound processor 1426 may use when processing sound from microphone 1426.

In an embodiment, the MAP for the bimodal hearing prosthesis 1400 may be determined using a genetic algorithm such as discussed above. For example, bimodal hearing prosthesis 1400 may be connected to a fitting system such as discussed above with reference to FIG. 9 that executes a method such as discussed above with reference to FIG. 11.

In yet another embodiment, rather than moving a portion of the recipient's inner ear 107, bimodal hearing prosthesis may use a transducer that mechanically moves a portion of the middle ear (e.g., incus 109) as noted above, or bimodal hearing prosthesis may use an air gap coupling for implantable transducers which are electromagnetic. For example, bimodal hearing prosthesis may comprise a hermetically tight transducer having a housing wall designed as a vibrating membrane which, together with a piezoelectric ceramic wafer applied to the inside thereof, comprises an electromechanically active composite element, the mechanical vibrations of which are transmitted to the ossicular chain via a coupling rod permanently attached to the outside of the membrane. Or, coupling rod may be attached to the membrane via a coupling element which is connected to the coupling rod. Or in another embodiment, a permanent magnet may be attached to the inside of the piezoelectric ceramic wafer to interact with an electromagnetic coil, such as an electromagnetic transducer. Such a combined piezoelectric-electromagnetic transducer is advantageous in particular with respect to a wide frequency band and achieving relatively high vibration amplitudes with comparatively small supplied energy. Or, in another embodiment, the transducer 150 may use a stapes prosthesis to mechanically move one or more of the semi-circular canals 165, which in turn generates fluid movement in cochlea 140. A further description of exemplary systems that may provide mechanical stimulation to a recipient's inner ear is provided in International Application No.: PCT/US09/38932, entitled "Objective Fitting of a Hearing Prosthesis," filed Mar. 31, 2009, the entire contents of which are hereby incorporated by reference.

The above-discussed cochlear implant systems may also be used in bilateral implant systems. For example, in embodiments, a cochlear implant system 100 may be fitted to both the right ear and left ear of a recipient to form a bilateral implant system. These cochlear implant systems in such a bilateral system may operate independently of one another, or, for example, may communicate either wireless or via a wired connection in delivering joint stimulation to the recipient. Or, for example, in yet another embodiment, a recipient may be fitted with a bone conduction device, such as a Bone-Anchored Hearing Aid (BAHA), on one ear, and a cochlear implant system on the other ear. As noted above, such a cochlear implant system may provide mechanical and/or electrical stimulation.

In embodiments, the above discussed exemplary mixed mode stimulating medical devices may be fitted using a fitting system such as discussed above with reference to FIG. 9 that uses a genetic algorithm in searching for a MAP for use by the stimulating medical device.

In cochlear implant systems which provide electrical and mechanical stimulation, additional parameters may be selected to tailor the cochlear implant system to an individual recipient. These parameters may include long term loudness balance (that is, electrical and mechanical gains), short term gain manipulations, particularly signal-dependent gain adjustments. Such gain adjustments include, for example, adjustments to minimize cross-modal masking, and adjustments to emphasize speech features such as noise, frication or voicing.

In yet another embodiment, a fitting system such as discussed above with reference to FIG. 9 may use a genetic algorithm in fitting a mixed mode stimulating medical device that provides mechanical stimulation via bone conduction. The electrical stimulation may be provided using a stimulating lead assembly, such as discussed above. The mechanical stimulation may be provided using systems similar to those used in a bone conduction device, such as a Baha.

Exemplary parameters that may be included in the MAP for application of stimulation via bone conduction may include the gain (also referred to the volume). This gain may be fixed across all frequencies, or, for example, in certain embodiments the bone conduction device may use a gain versus frequency curve in which the gain varies by frequency.

In embodiment, the amplitude and shape of such a curve may be selected for use in applying stimulation via bone conduction may also be specified by the MAP. For example, the bone conduction processing may be able to implement a variety of gain curve shapes, such as one that emphasizes lower frequency sounds, one that emphasizes higher frequency sounds, one that emphasizes mid frequency sounds, and a flat curve that emphasizes all sounds equally. In such an embodiment, the MAP may comprise a parameter specifying the particular shape of the gain curve. Or, in yet other examples, the parameters for bone conduction may include other parameters, such as, for example, one or more transfer functions.

In another embodiment, other methods and system may be used in executing a genetic algorithm in determining a MAP for use by a mixed mode stimulating medical device. For example, an embodiment, the fitting system may employ a genetic algorithm search such as discloses in U.S. patent application Ser. No. 12/557,208 entitled "Using a Genetic Algorithm to Fit a Medical Implant System to a Patient," which is hereby incorporated by reference. For example, in embodiments, rather than using bit string representations of the MAPs, in other embodiments MAPs may be used that include data structures in which the actual parameter values are stored. Or, for example, alternative mechanisms for parent selection may be used, such as, for example, the recipient may sequentially listen to a sound token processed by each of the MAPs, where the fitting system plays a unique sound token for each provided MAP. Then, the recipient may determine which of the audible signals and corresponding MAPs sounded the clearest. Or, in another embodiment, the recipient need not select a particular number of MAPs that sounded the clearest, but instead, may simply identify the provided MAPs that the recipient considered good.

In yet another embodiment, rather than the fitting system asking the recipient whether the sound perception was good or not, the fitting system may ask the recipient what they heard. And, then fitting system may identify the corresponding MAP as good if the recipient correctly identifies the sound token. For example, in an embodiment, the sound tokens may comprise spoken phrases. Then, fitting system may present a graphical user interface (GUI) to the recipient via display that lets the recipient select a graphical list of possible phrases. If the recipient selects the correct phrase, the corresponding MAP may be deemed good, while if the incorrect phrase was selected, the corresponding MAP may be deemed bad. That is, if the correct phrase is identified, fitting system may select the corresponding MAP at block. While, if the correct phrase is not identified, fitting system 206 may not select the corresponding MAP at block 1108.

It should be noted that although the above-discussed embodiments were discussed with reference to a cochlear implant, in other embodiments a fitting system may be used to permit a recipient to measure the dynamic range of other stimulating medical devices, such as, for example, bone conduction devices, auditory brain stimulators, etc.

Various implementations of the subject matter described, such as the embodiment of FIG. 2, components of may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for at least partially fitting a medical implant system comprising a system for providing multiple modes of stimulation to a recipient, wherein each mode of stimulation comprises at least one fitting parameter, the method comprising:
  executing a genetic algorithm to select a determined value set comprising values for at least one fitting parameter for electrical stimulation and at least one parameter for another mode of stimulation, the genetic algorithm comprising:
    presenting signals processed by a plurality of value sets to the recipient using the medical implant system;
    receiving recipient feedback in response to the presented signals processed by the value sets;
    selecting, based on the recipient feedback, one or more of the presented value sets; and
    generating a successive generation of value sets using the selected one or more value sets; and
  providing the determined value set to the medical implant system for use in providing electrical and the other mode stimulation to the recipient.

2. The method of claim 1, wherein the electrical mode of stimulation is provided by an electrical stimulation system comprising an electrode array configured to provide electrical stimulation to a cochlea of the recipient.

3. The method of claim 1, wherein the other mode of stimulation comprises acoustic stimulation provided by loudspeaker.

4. The method of claim 3, wherein at least one of the fitting parameters comprises a first cutoff frequency specifying a maximum frequency for which acoustic stimulation is to be provided to the recipient.

5. The method of claim 4, wherein the at least another one of the fitting parameters comprises a second cutoff frequency specifying a minimum frequency for which electrical stimulation is to be provided to the recipient.

6. The method of claim 4, wherein the first cutoff frequency further specifies a minimum frequency for which electrical stimulation is to be provided to the recipient.

7. The method of claim 1, wherein the other mode of simulation comprises providing mechanical stimulation to a middle ear of the recipient.

8. The method of claim 1, wherein the other mode of simulation comprises providing mechanical stimulation to an inner ear of the recipient.

9. The method of claim 1, wherein the other mode of stimulation comprises providing mechanical stimulation system via bone conduction.

10. The method of claim 9, wherein the at least one fitting parameter comprises a gain to be applied in providing mechanical stimulation via bone conduction.

11. The method of claim 10, wherein the at least one fitting parameter further comprises a gain curve shape for use in providing mechanical stimulation via bone conduction.

12. The method of claim 1, wherein the electrical and other mode of stimulation are provided to the same ear of a recipient.

13. The method of claim 1, wherein presenting a plurality of value sets comprises:
providing a value for at least one parameter for electrical stimulation;
providing a value for at least one parameter for the other mode of stimulation; and
providing an audible signal to the recipient;
processing the audible signal by an electrical stimulation system using the value for electrical stimulation; and
processing the audible signal by another stimulation system using the value provided for the other mode of stimulation.

14. The method of claim 1, wherein the electrical stimulation is provided to a first ear of the recipient and the other mode of stimulation is provided to a second ear of the recipient.

15. A system for at least partially fitting a mixed mode medical implant system to a recipient, wherein the mixed mode medical implant system is configured to provide electrical stimulation and an other mode of stimulation to the recipient, the system comprising:
a processor configured to execute a genetic algorithm to select a determined value set comprising values for at least one parameter for providing electrical stimulation and at least one parameter for providing the other mode of stimulation, wherein the processor in executing the genetic algorithm is configured to present signals processed by a plurality of value sets to the recipient using the medical implant system, receive recipient feedback in response to the presented signals, select, based on the recipient feedback, one or more of the value sets, and generate a successive generation of value sets using the selected one or more value sets; and
an interface configured to provide at least one of the value sets to the medical implant system for use by the medical implant system in providing stimulation to the recipient.

16. The system of claim 15, wherein medical implant system comprises an electrical stimulation system comprising an electrode array configured to provide electrical stimulation to a cochlea of the recipient.

17. The system of claim 15, wherein the medical implant system comprises an acoustic stimulation system comprising a loudspeaker.

18. The system of claim 15, wherein at least one of the fitting parameters comprises a first cutoff frequency specifying a maximum frequency for which acoustic stimulation is to be provided to the recipient.

19. The system of claim 18, wherein the at least another one of the fitting parameters comprises a second cutoff frequency specifying a minimum frequency for which electrical stimulation is to be provided to the recipient.

20. The system of claim 18, wherein the first cutoff frequency further specifies a minimum frequency for which electrical stimulation is to be provided to the recipient.

21. The system of claim 19, wherein the at least one fitting parameter comprises a gain to be applied in providing mechanical stimulation via bone conduction.

22. The system of claim 20, wherein the at least one fitting parameter further comprises a gain curve shape for use in providing mechanical stimulation via bone conduction.

23. The system of claim 15, wherein the medical implant system comprises a mechanical stimulation system configured to provide mechanical stimulation to a middle ear of the recipient.

24. The system of claim 15, wherein the medical implant system comprises a mechanical stimulation system configured provide mechanical stimulation to an inner ear of the recipient.

25. The system of claim 15, wherein the medical implant system comprises a mechanical stimulation system configured provide mechanical stimulation via bone conduction.

26. The system of claim 15, wherein the medical implant system is configured to provide electrical and other mode of stimulation to the same ear of a recipient.

27. The system of claim 15, wherein the medical implant system is configured to provide electrical stimulation to a first ear of the recipient and the other mode of stimulation to a second ear of the recipient.

28. A system for at least partially fitting a medical implant system for providing multiple modes of stimulation to a recipient, wherein each mode of stimulation comprises at least one fitting parameter, the system comprising:
selection means for executing a genetic algorithm to select a determined value set comprising values for at least one fitting parameter for electrical stimulation and at least one parameter for another mode of stimulation, the selection means including:
means for presenting signals processed by a plurality of value sets to the recipient using the medical implant system;
means for receiving recipient feedback in response to the presented signals processed by the value sets;
means for selecting, based on the recipient feedback, one or more of the presented value sets; and
means for generating a successive generation of value sets using the selected one or more value sets; and
means for providing the determined value set to the medical implant system for use in providing electrical and the other mode stimulation to the recipient.

* * * * *